US008858613B2

(12) United States Patent
Cragg et al.

(10) Patent No.: US 8,858,613 B2
(45) Date of Patent: Oct. 14, 2014

(54) STENT GRAFT DELIVERY SYSTEMS AND ASSOCIATED METHODS

(75) Inventors: Andrew H. Cragg, Edina, MN (US); Isa Rizk, San Diego, CA (US); Stephen Sosnowski, Vista, CA (US); John Logan, Plymouth, MN (US); Mahmood Dehdashtian, Costa Mesa, CA (US); Pedram Nourian, Dana Point, CA (US)

(73) Assignee: Altura Medical, Inc., Menlo Park, CA (US)

( * ) Notice: Subject to any disclaimer, the term of this patent is extended or adjusted under 35 U.S.C. 154(b) by 89 days.

(21) Appl. No.: 13/237,822

(22) Filed: Sep. 20, 2011

(65) Prior Publication Data

US 2012/0130469 A1    May 24, 2012

Related U.S. Application Data

(60) Provisional application No. 61/384,669, filed on Sep. 20, 2010, provisional application No. 61/527,064, filed on Aug. 24, 2011.

(51) Int. Cl.
| | |
|---|---|
| *A61F 2/06* | (2013.01) |
| *A61F 2/954* | (2013.01) |
| *A61F 2/90* | (2013.01) |
| *A61F 2/966* | (2013.01) |
| *A61F 2/07* | (2013.01) |

(52) U.S. Cl.
CPC ........... *A61F 2/954* (2013.01); *A61F 2002/067* (2013.01); *A61F 2002/9665* (2013.01); *A61F 2002/075* (2013.01); *A61F 2/07* (2013.01); *A61F 2230/0034* (2013.01); *A61F 2/90* (2013.01)
USPC ........................................ 623/1.12; 623/1.11

(58) Field of Classification Search
CPC ............. A61F 2/07; A61F 2/90; A61F 2/645; A61F 2002/07; A61F 2002/072; A61F 2002/075; A61F 2002/077
USPC ................ 606/191, 192, 198; 623/1.13, 1.14, 623/1.16, 1.23, 1.35, 1.36, 1.44
See application file for complete search history.

(56) References Cited

U.S. PATENT DOCUMENTS

| | | | |
|---|---|---|---|
| 4,562,596 A |  | 1/1986 | Kornberg |
| 4,990,151 A | * | 2/1991 | Wallsten ....................... 606/108 |

(Continued)

FOREIGN PATENT DOCUMENTS

| | | |
|---|---|---|
| CN | 1272053 | 11/2000 |
| EP | 808613 A1 | 11/1997 |

(Continued)

OTHER PUBLICATIONS

Beebe, H.G.; "Imaging Modalities for Aortic Endografting"; J Endovasc Surg; May 1997; vol. 4, Issue 2, pp. 111-123 (20 pages).

(Continued)

*Primary Examiner* — Tuan V Nguyen
(74) *Attorney, Agent, or Firm* — Perkins Coie LLP

(57) ABSTRACT

Stent graft delivery systems are disclosed herein. In several embodiments, a stent graft delivery system can include a stent graft having a proximal portion and a distal portion, a proximal sheath and a distal sheath. The proximal sheath can be configured to cover the proximal portion of the stent graft, and the distal sheath can be configured to cover the distal portion of the stent graft. The proximal sheath and the distal sheath can be independently removable from respective ends of the stent graft such that the proximal and distal portions of the stent graft are independently deployable.

16 Claims, 10 Drawing Sheets

(56) References Cited

U.S. PATENT DOCUMENTS

| | | |
|---|---|---|
| 5,078,726 A | 1/1992 | Kreamer |
| 5,201,757 A | 4/1993 | Heyn et al. |
| 5,316,023 A | 5/1994 | Palmaz et al. |
| 5,360,443 A | 11/1994 | Barone et al. |
| 5,364,352 A | 11/1994 | Cimino et al. |
| 5,397,345 A | 3/1995 | Lazarus |
| 5,415,664 A | 5/1995 | Pinchuk |
| 5,433,723 A | 7/1995 | Lindenberg et al. |
| 5,445,646 A * | 8/1995 | Euteneuer et al. ............ 606/198 |
| 5,464,449 A | 11/1995 | Ryan et al. |
| 5,476,505 A | 12/1995 | Limon |
| 5,476,506 A | 12/1995 | Lunn |
| 5,480,423 A | 1/1996 | Ravenscroft et al. |
| 5,507,731 A | 4/1996 | Hernandez et al. |
| 5,507,769 A | 4/1996 | Marin et al. |
| 5,522,880 A | 6/1996 | Barone et al. |
| 5,562,724 A | 10/1996 | Vorwerk et al. |
| 5,571,170 A | 11/1996 | Palmaz et al. |
| 5,571,171 A | 11/1996 | Barone et al. |
| 5,571,173 A | 11/1996 | Parodi |
| 5,578,071 A | 11/1996 | Parodi |
| 5,578,072 A | 11/1996 | Barone et al. |
| 5,591,195 A | 1/1997 | Taheri et al. |
| 5,591,228 A | 1/1997 | Edoga |
| 5,591,229 A | 1/1997 | Parodi |
| 5,609,627 A | 3/1997 | Goicoechea et al. |
| 5,628,783 A | 5/1997 | Quiachon et al. |
| 5,628,788 A | 5/1997 | Pinchuk |
| 5,632,763 A | 5/1997 | Glastra |
| 5,632,772 A | 5/1997 | Alcime et al. |
| 5,639,278 A | 6/1997 | Dereume et al. |
| 5,653,743 A | 8/1997 | Martin |
| 5,662,606 A | 9/1997 | Cimino et al. |
| 5,683,450 A | 11/1997 | Goicoechea et al. |
| 5,683,453 A | 11/1997 | Palmaz |
| 5,693,084 A | 12/1997 | Chuter |
| 5,693,087 A | 12/1997 | Parodi |
| 5,707,376 A | 1/1998 | Kavteladze et al. |
| 5,713,917 A | 2/1998 | Leonhardt et al. |
| 5,716,365 A | 2/1998 | Goicoechea et al. |
| 5,755,734 A | 5/1998 | Richter et al. |
| 5,755,735 A | 5/1998 | Richter et al. |
| 5,755,770 A | 5/1998 | Ravenscroft |
| 5,759,186 A | 6/1998 | Bachmann et al. |
| 5,776,142 A | 7/1998 | Gunderson |
| 5,824,041 A | 10/1998 | Lenker et al. |
| 5,824,058 A | 10/1998 | Ravenscroft et al. |
| 5,833,694 A | 11/1998 | Poncet |
| 5,843,160 A | 12/1998 | Rhodes |
| 5,855,598 A | 1/1999 | Pinchuk |
| 5,871,536 A | 2/1999 | Lazarus |
| 5,897,587 A | 4/1999 | Martakos et al. |
| 5,904,713 A | 5/1999 | Leschinsky |
| 5,906,619 A | 5/1999 | Olson et al. |
| 5,916,263 A | 6/1999 | Goicoechea et al. |
| 5,928,279 A | 7/1999 | Shannon et al. |
| 5,968,068 A | 10/1999 | Dehdashtian et al. |
| 5,984,955 A | 11/1999 | Wisselink |
| 5,984,964 A | 11/1999 | Roberts et al. |
| 5,993,481 A | 11/1999 | Marcade et al. |
| 6,001,125 A | 12/1999 | Golds et al. |
| 6,004,348 A | 12/1999 | Banas et al. |
| 6,015,431 A | 1/2000 | Thornton et al. |
| 6,019,778 A | 2/2000 | Wilson et al. |
| 6,024,763 A | 2/2000 | Lenker et al. |
| 6,039,749 A | 3/2000 | Marin et al. |
| 6,042,589 A | 3/2000 | Marianne |
| 6,051,020 A | 4/2000 | Goicoechea et al. |
| 6,053,899 A | 4/2000 | Slanda et al. |
| 6,060,128 A | 5/2000 | Kim et al. |
| 6,070,589 A | 6/2000 | Keith et al. |
| 6,077,296 A | 6/2000 | Shokoohi et al. |
| 6,090,128 A | 7/2000 | Douglas |
| 6,090,133 A | 7/2000 | Richter et al. |
| 6,099,558 A | 8/2000 | White et al. |
| 6,102,940 A | 8/2000 | Robichon et al. |
| 6,117,156 A | 9/2000 | Richter et al. |
| 6,117,167 A | 9/2000 | Goicoechea et al. |
| 6,120,522 A | 9/2000 | Vrba et al. |
| 6,126,685 A | 10/2000 | Lenker et al. |
| 6,129,756 A | 10/2000 | Kugler et al. |
| 6,146,415 A | 11/2000 | Fitz |
| 6,156,063 A | 12/2000 | Douglas |
| 6,162,237 A | 12/2000 | Chan |
| 6,162,246 A | 12/2000 | Barone |
| 6,165,213 A | 12/2000 | Goicoechea et al. |
| 6,168,610 B1 | 1/2001 | Marin et al. |
| 6,168,616 B1 | 1/2001 | Brown, III |
| 6,171,277 B1 | 1/2001 | Ponzi |
| 6,174,330 B1 * | 1/2001 | Stinson ........................ 623/1.34 |
| 6,179,809 B1 | 1/2001 | Khairkhahan et al. |
| 6,183,444 B1 | 2/2001 | Glines et al. |
| 6,183,481 B1 | 2/2001 | Lee et al. |
| 6,187,036 B1 | 2/2001 | Shaolian et al. |
| 6,197,049 B1 | 3/2001 | Shaolian et al. |
| 6,200,339 B1 | 3/2001 | Leschinsky et al. |
| 6,203,550 B1 | 3/2001 | Olson |
| 6,210,422 B1 | 4/2001 | Douglas |
| 6,217,609 B1 | 4/2001 | Haverkost |
| 6,221,102 B1 | 4/2001 | Baker et al. |
| 6,230,476 B1 | 5/2001 | Carr et al. |
| 6,231,597 B1 | 5/2001 | Deem et al. |
| 6,238,402 B1 | 5/2001 | Sullivan, III et al. |
| 6,261,316 B1 | 7/2001 | Shaolian et al. |
| 6,267,783 B1 | 7/2001 | Letendre et al. |
| 6,270,525 B1 | 8/2001 | Letendre et al. |
| 6,290,731 B1 | 9/2001 | Solovay et al. |
| 6,302,906 B1 | 10/2001 | Goicoechea et al. |
| 6,306,141 B1 | 10/2001 | Jervis |
| 6,306,164 B1 | 10/2001 | Kujawski |
| 6,306,424 B1 | 10/2001 | Vyakarnam et al. |
| 6,309,413 B1 | 10/2001 | Dereume et al. |
| 6,325,819 B1 | 12/2001 | Pavcnik et al. |
| 6,325,822 B1 | 12/2001 | Chouinard et al. |
| 6,331,190 B1 | 12/2001 | Shokoohi et al. |
| 6,331,191 B1 | 12/2001 | Chobotov |
| 6,344,052 B1 | 2/2002 | Greenan et al. |
| 6,344,056 B1 | 2/2002 | Dehdashtian |
| 6,371,963 B1 | 4/2002 | Nishtala et al. |
| 6,383,193 B1 | 5/2002 | Cathcart et al. |
| 6,391,033 B2 | 5/2002 | Ryan |
| 6,391,051 B2 | 5/2002 | Sullivan, III et al. |
| 6,395,019 B2 | 5/2002 | Chobotov |
| 6,398,802 B1 * | 6/2002 | Yee ........................ 623/1.13 |
| 6,398,807 B1 | 6/2002 | Chouinard et al. |
| 6,409,750 B1 | 6/2002 | Hyodoh et al. |
| 6,416,542 B1 | 7/2002 | Marcade et al. |
| 6,468,260 B1 | 10/2002 | Bumbalough et al. |
| 6,478,813 B1 | 11/2002 | Keith et al. |
| 6,482,227 B1 | 11/2002 | Solovay |
| 6,488,700 B2 | 12/2002 | Klumb et al. |
| 6,500,203 B1 | 12/2002 | Thompson et al. |
| 6,514,261 B1 | 2/2003 | Randall et al. |
| 6,517,571 B1 | 2/2003 | Brauker et al. |
| 6,517,572 B2 | 2/2003 | Kugler et al. |
| 6,517,574 B1 | 2/2003 | Chuter |
| 6,520,983 B1 | 2/2003 | Colgan et al. |
| 6,524,336 B1 | 2/2003 | Papazolgou et al. |
| 6,533,811 B1 | 3/2003 | Ryan et al. |
| 6,554,794 B1 | 4/2003 | Mueller et al. |
| 6,554,858 B2 | 4/2003 | Dereume et al. |
| RE38,146 E | 6/2003 | Palmaz et al. |
| 6,572,643 B1 | 6/2003 | Gharibadeh |
| 6,576,006 B2 | 6/2003 | Limon et al. |
| 6,585,756 B1 | 7/2003 | Strecker |
| 6,602,225 B2 | 8/2003 | Eidenschink et al. |
| 6,602,280 B2 | 8/2003 | Chobotov |
| 6,629,981 B2 | 10/2003 | Bui et al. |
| 6,645,242 B1 | 11/2003 | Quinn |
| 6,652,567 B1 | 11/2003 | Deaton |
| 6,656,215 B1 | 12/2003 | Yanez et al. |
| 6,660,030 B2 | 12/2003 | Shaolian et al. |
| 6,663,645 B2 | 12/2003 | Nishtala et al. |
| 6,682,557 B1 | 1/2004 | Quiachon et al. |

(56) References Cited

U.S. PATENT DOCUMENTS

| | | |
|---|---|---|
| 6,695,875 B2 | 2/2004 | Stelter et al. |
| 6,730,119 B1 | 5/2004 | Smalling |
| 6,733,521 B2 | 5/2004 | Chobotov et al. |
| 6,743,247 B1 | 6/2004 | Levinson et al. |
| 6,755,854 B2 | 6/2004 | Gillick et al. |
| 6,761,733 B2 | 7/2004 | Chobotov et al. |
| 6,773,457 B2 | 8/2004 | Ivancev et al. |
| 6,786,920 B2 | 9/2004 | Shannon et al. |
| 6,790,225 B1 | 9/2004 | Shannon et al. |
| 6,792,979 B2 | 9/2004 | Konya et al. |
| 6,808,529 B2 | 10/2004 | Fulkerson |
| 6,808,533 B1 | 10/2004 | Goodwin et al. |
| 6,808,534 B1 | 10/2004 | Escano |
| 6,814,752 B1 | 11/2004 | Chuter |
| 6,830,575 B2 | 12/2004 | Stenzel et al. |
| 6,843,802 B1 | 1/2005 | Villalobos et al. |
| 6,843,803 B2 | 1/2005 | Ryan et al. |
| 6,849,084 B2 | 2/2005 | Rabkin et al. |
| 6,858,038 B2 | 2/2005 | Heuser |
| 6,866,669 B2 | 3/2005 | Buzzard et al. |
| 6,878,164 B2 | 4/2005 | Kujawski et al. |
| 6,887,268 B2 | 5/2005 | Butaric et al. |
| 6,911,039 B2 | 6/2005 | Shiu et al. |
| 6,913,594 B2 | 7/2005 | Coleman et al. |
| 6,926,724 B1 | 8/2005 | Chu |
| 6,929,661 B2 | 8/2005 | Bolduc et al. |
| 6,939,352 B2 | 9/2005 | Buzzard et al. |
| 6,939,371 B2 | 9/2005 | Kugler et al. |
| 6,942,691 B1 | 9/2005 | Chuter |
| 6,942,692 B2 | 9/2005 | Landau et al. |
| 6,951,572 B1 | 10/2005 | Douglas |
| 6,964,679 B1 | 11/2005 | Marcade et al. |
| 6,974,471 B2 | 12/2005 | Van Schie et al. |
| 6,981,982 B2 | 1/2006 | Armstrong et al. |
| 6,984,243 B2 | 1/2006 | Dwyer et al. |
| 6,984,244 B2 | 1/2006 | Perez et al. |
| 7,000,649 B2 | 2/2006 | Takahashi et al. |
| 7,001,423 B2 | 2/2006 | Euteneuer et al. |
| 7,014,653 B2 | 3/2006 | Ouriel et al. |
| 7,018,401 B1 | 3/2006 | Hyodoh et al. |
| 7,048,014 B2 | 5/2006 | Hyodoh et al. |
| 7,052,511 B2 * | 5/2006 | Weldon et al. ............ 623/1.11 |
| 7,052,513 B2 | 5/2006 | Thompson |
| 7,063,721 B2 | 6/2006 | Takahashi et al. |
| 7,074,236 B2 | 7/2006 | Rabkin et al. |
| 7,105,016 B2 | 9/2006 | Shiu et al. |
| 7,112,217 B1 | 9/2006 | Kugler et al. |
| 7,118,592 B1 | 10/2006 | Dang et al. |
| 7,122,050 B2 | 10/2006 | Randall et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 * | 1/2007 | Greenberg et al. ......... 623/1.13 |
| 7,169,118 B2 | 1/2007 | Reynolds et al. |
| 7,175,651 B2 | 2/2007 | Kerr |
| 7,220,274 B1 | 5/2007 | Quinn |
| 7,226,474 B2 | 6/2007 | Iancea et al. |
| 7,229,472 B2 | 6/2007 | DePalma et al. |
| 7,232,459 B2 | 6/2007 | Greenberg et al. |
| 7,238,197 B2 | 7/2007 | Sequin et al. |
| 7,264,631 B2 | 9/2007 | DiCarlo |
| 7,264,632 B2 | 9/2007 | Wright et al. |
| 7,267,685 B2 | 9/2007 | Butaric et al. |
| 7,278,998 B2 | 10/2007 | Gaschino et al. |
| 7,294,147 B2 | 11/2007 | Hartley |
| 7,306,623 B2 | 12/2007 | Watson |
| 7,314,483 B2 | 1/2008 | Landau et al. |
| 7,314,484 B2 | 1/2008 | Deem et al. |
| 7,318,835 B2 | 1/2008 | Berra |
| 7,326,237 B2 | 2/2008 | DePalma et al. |
| 7,344,562 B2 | 3/2008 | Feller et al. |
| 7,357,812 B2 | 4/2008 | Andreas et al. |
| 7,371,255 B2 | 5/2008 | Richter et al. |
| RE40,404 E | 6/2008 | Schmitt et al. |
| 7,402,163 B2 | 7/2008 | Nishtala et al. |
| 7,435,253 B1 | 10/2008 | Hartley et al. |
| 7,476,244 B2 | 1/2009 | Buzzard et al. |
| 7,481,836 B2 | 1/2009 | Greenan |
| 7,488,344 B2 | 2/2009 | Hartley et al. |
| 7,517,361 B1 | 4/2009 | Ravenscroft |
| RE40,816 E | 6/2009 | Taylor et al. |
| 7,550,004 B2 | 6/2009 | Bahler et al. |
| 7,575,591 B2 | 8/2009 | Howat et al. |
| 7,588,596 B2 | 9/2009 | Spiridigliozzi et al. |
| 7,615,044 B2 | 11/2009 | Scheibe et al. |
| 7,615,071 B2 | 11/2009 | Chobotov |
| 7,655,034 B2 | 2/2010 | Mitchell et al. |
| 7,655,040 B2 | 2/2010 | Douk et al. |
| 7,674,282 B2 | 3/2010 | Wu et al. |
| 7,678,141 B2 | 3/2010 | Greenan et al. |
| 7,682,381 B2 | 3/2010 | Rakos et al. |
| 7,691,109 B2 | 4/2010 | Armstrong et al. |
| 7,691,138 B2 | 4/2010 | Stenzel et al. |
| 7,695,506 B2 | 4/2010 | Thistle et al. |
| 7,708,771 B2 | 5/2010 | Chuter et al. |
| 7,766,960 B2 | 8/2010 | Alexander et al. |
| 7,766,961 B2 | 8/2010 | Patel et al. |
| 7,780,717 B2 | 8/2010 | Ducke et al. |
| 7,828,833 B2 | 11/2010 | Haverkost et al. |
| 7,828,838 B2 | 11/2010 | Bolduc et al. |
| 7,837,724 B2 | 11/2010 | Keeble et al. |
| 7,862,609 B2 | 1/2011 | Butaric et al. |
| 7,887,576 B2 | 2/2011 | Bahler et al. |
| 7,918,880 B2 | 4/2011 | Austin |
| 7,935,140 B2 | 5/2011 | Griffin |
| 7,938,852 B2 | 5/2011 | Andreas et al. |
| 7,993,384 B2 | 8/2011 | Wu et al. |
| 8,021,410 B2 | 9/2011 | Melsheimer |
| 8,025,692 B2 | 9/2011 | Feeser |
| 8,075,606 B2 | 12/2011 | Dorn |
| 8,114,147 B2 | 2/2012 | Wood et al. |
| 8,136,004 B2 | 3/2012 | Umesh et al. |
| 8,163,004 B2 | 4/2012 | Amplatz et al. |
| 8,164,892 B2 | 4/2012 | An |
| 8,167,892 B2 | 5/2012 | Feller, III et al. |
| 8,187,291 B2 | 5/2012 | Nishtala et al. |
| 8,241,344 B2 | 8/2012 | Kusleika et al. |
| 8,287,583 B2 | 10/2012 | LaDuca et al. |
| 8,323,239 B2 | 12/2012 | Bednarek et al. |
| 8,357,190 B2 | 1/2013 | Fearn et al. |
| 8,372,131 B2 | 2/2013 | Hestad et al. |
| 8,434,393 B2 | 5/2013 | Adams |
| 8,470,015 B2 | 6/2013 | Barthold |
| 8,486,128 B2 | 7/2013 | Jen et al. |
| 2001/0014823 A1 | 8/2001 | Ressemann et al. |
| 2002/0013620 A1 | 1/2002 | Kujawski |
| 2002/0019659 A1 | 2/2002 | Goicoechea et al. |
| 2002/0019664 A1 | 2/2002 | Douglas |
| 2002/0143387 A1 | 10/2002 | Soetikno et al. |
| 2002/0151933 A1 | 10/2002 | Sheldon |
| 2002/0169497 A1 | 11/2002 | Wholey et al. |
| 2003/0014075 A1 | 1/2003 | Rosenbluth et al. |
| 2003/0130720 A1 | 7/2003 | DePalma et al. |
| 2003/0130725 A1 | 7/2003 | DePalma et al. |
| 2003/0199967 A1 | 10/2003 | Hartley et al. |
| 2003/0199973 A1 | 10/2003 | Chuter et al. |
| 2004/0019375 A1 | 1/2004 | Casey et al. |
| 2004/0054397 A1 | 3/2004 | Smith et al. |
| 2004/0059406 A1 | 3/2004 | Cully et al. |
| 2004/0073288 A1 | 4/2004 | Kerr |
| 2004/0098092 A1 | 5/2004 | Butaric et al. |
| 2004/0117003 A1 | 6/2004 | Ouriel et al. |
| 2004/0138734 A1 | 7/2004 | Chobotov et al. |
| 2004/0143316 A1 | 7/2004 | Spiridigliozzi et al. |
| 2004/0162604 A1 | 8/2004 | Sowinski et al. |
| 2004/0193245 A1 | 9/2004 | Deem et al. |
| 2004/0193252 A1 | 9/2004 | Perez et al. |
| 2004/0215316 A1 | 10/2004 | Smalling |
| 2004/0230289 A1 | 11/2004 | DiMatteo et al. |
| 2004/0236406 A1 | 11/2004 | Gregorich |
| 2004/0260382 A1 | 12/2004 | Fogarty et al. |
| 2005/0021123 A1 | 1/2005 | Dorn et al. |
| 2005/0033400 A1 | 2/2005 | Chuter |
| 2005/0033416 A1 | 2/2005 | Seguin et al. |

(56) References Cited

U.S. PATENT DOCUMENTS

| | | |
|---|---|---|
| 2005/0043780 A1 | 2/2005 | Gifford et al. |
| 2005/0085894 A1 | 4/2005 | Kershner |
| 2005/0113906 A9 | 5/2005 | Bolduc et al. |
| 2005/0119721 A1* | 6/2005 | Rabkin et al. ............... 623/1.12 |
| 2005/0131516 A1 | 6/2005 | Greenhalgh |
| 2005/0137677 A1 | 6/2005 | Rush |
| 2005/0143804 A1 | 6/2005 | Haverkost |
| 2005/0154441 A1* | 7/2005 | Schaeffer et al. ............ 623/1.11 |
| 2005/0171598 A1 | 8/2005 | Schaeffer |
| 2005/0222668 A1 | 10/2005 | Schaeffer et al. |
| 2005/0228475 A1 | 10/2005 | Keeble et al. |
| 2005/0228484 A1 | 10/2005 | Stephens et al. |
| 2005/0273154 A1 | 12/2005 | Colone |
| 2005/0288772 A1 | 12/2005 | Douglas |
| 2006/0030921 A1 | 2/2006 | Chu |
| 2006/0058864 A1 | 3/2006 | Schaeffer et al. |
| 2006/0074481 A1 | 4/2006 | Vardi et al. |
| 2006/0085057 A1 | 4/2006 | George et al. |
| 2006/0095116 A1 | 5/2006 | Bolduc et al. |
| 2006/0142694 A1 | 6/2006 | Bednarek et al. |
| 2006/0155359 A1 | 7/2006 | Watson |
| 2006/0155366 A1 | 7/2006 | LaDuca et al. |
| 2006/0161244 A1 | 7/2006 | Seguin |
| 2006/0178733 A1 | 8/2006 | Pinchuk et al. |
| 2006/0212112 A1 | 9/2006 | Evans et al. |
| 2006/0224232 A1 | 10/2006 | Chobotov |
| 2006/0233990 A1 | 10/2006 | Humphrey et al. |
| 2006/0265055 A1 | 11/2006 | Lauterjung |
| 2006/0282155 A1 | 12/2006 | Fearn et al. |
| 2007/0032852 A1 | 2/2007 | Machek et al. |
| 2007/0051377 A1 | 3/2007 | Douk et al. |
| 2007/0055341 A1 | 3/2007 | Edoga et al. |
| 2007/0055360 A1 | 3/2007 | Hanson et al. |
| 2007/0055363 A1 | 3/2007 | Chuter et al. |
| 2007/0100429 A1* | 5/2007 | Wu et al. ..................... 623/1.11 |
| 2007/0118208 A1 | 5/2007 | Kerr |
| 2007/0142895 A1 | 6/2007 | Castaneda et al. |
| 2007/0142896 A1 | 6/2007 | Anderson et al. |
| 2007/0150041 A1 | 6/2007 | Evans et al. |
| 2007/0156224 A1 | 7/2007 | Cioanta et al. |
| 2007/0156229 A1 | 7/2007 | Park |
| 2007/0162109 A1 | 7/2007 | Davila et al. |
| 2007/0168017 A1 | 7/2007 | Sarac |
| 2007/0168018 A1 | 7/2007 | Amplatz et al. |
| 2007/0173929 A1 | 7/2007 | Boucher et al. |
| 2007/0179592 A1 | 8/2007 | Schaeffer |
| 2007/0179600 A1 | 8/2007 | Vardi |
| 2007/0198077 A1 | 8/2007 | Cully et al. |
| 2007/0198079 A1 | 8/2007 | Casey et al. |
| 2007/0219620 A1 | 9/2007 | Eells et al. |
| 2007/0225797 A1 | 9/2007 | Krivoruhko |
| 2007/0233220 A1 | 10/2007 | Greenan |
| 2007/0233222 A1 | 10/2007 | Roeder et al. |
| 2007/0244542 A1 | 10/2007 | Greenan et al. |
| 2007/0244547 A1 | 10/2007 | Greenan |
| 2007/0265697 A1 | 11/2007 | Goicoechea et al. |
| 2007/0293940 A1 | 12/2007 | Schaeffer et al. |
| 2008/0015682 A1 | 1/2008 | Majercak et al. |
| 2008/0046065 A1 | 2/2008 | Hartley et al. |
| 2008/0082154 A1 | 4/2008 | Tseng et al. |
| 2008/0082158 A1 | 4/2008 | Tseng et al. |
| 2008/0082159 A1 | 4/2008 | Tseng et al. |
| 2008/0097572 A1 | 4/2008 | Sheldon et al. |
| 2008/0108969 A1 | 5/2008 | Kerr |
| 2008/0114435 A1 | 5/2008 | Bowe |
| 2008/0114444 A1 | 5/2008 | Yu |
| 2008/0114449 A1 | 5/2008 | Gregorich et al. |
| 2008/0125847 A1 | 5/2008 | Krever et al. |
| 2008/0132993 A1 | 6/2008 | Rasmussen et al. |
| 2008/0167704 A1 | 7/2008 | Wright et al. |
| 2008/0183272 A1 | 7/2008 | Wood et al. |
| 2008/0195191 A1 | 8/2008 | Luo et al. |
| 2008/0208325 A1 | 8/2008 | Helmus et al. |
| 2008/0221659 A1 | 9/2008 | Hartley et al. |
| 2008/0221668 A1 | 9/2008 | Pinchuk et al. |
| 2008/0249601 A1 | 10/2008 | Kerr |
| 2008/0262595 A1 | 10/2008 | Chu et al. |
| 2008/0290076 A1 | 11/2008 | Sheldon et al. |
| 2009/0030501 A1 | 1/2009 | Morris et al. |
| 2009/0036973 A1 | 2/2009 | Humphrey et al. |
| 2009/0043376 A1 | 2/2009 | Hamer et al. |
| 2009/0099647 A1 | 4/2009 | Glimsdale et al. |
| 2009/0099649 A1 | 4/2009 | Chobotov et al. |
| 2009/0105640 A1 | 4/2009 | Bednarek et al. |
| 2009/0125095 A1 | 5/2009 | Bui et al. |
| 2009/0138067 A1 | 5/2009 | Pinchuk et al. |
| 2009/0164001 A1 | 6/2009 | Biggs et al. |
| 2009/0171451 A1 | 7/2009 | Kuppurathanam et al. |
| 2009/0173439 A1 | 7/2009 | Hayashi et al. |
| 2009/0177265 A1 | 7/2009 | Dierking et al. |
| 2009/0182413 A1 | 7/2009 | Burkart et al. |
| 2009/0187240 A1 | 7/2009 | Clerc et al. |
| 2009/0228020 A1 | 9/2009 | Wallace et al. |
| 2009/0248144 A1 | 10/2009 | Bahler et al. |
| 2009/0264992 A1 | 10/2009 | Fleming, III et al. |
| 2009/0276035 A1 | 11/2009 | Waysbeyn et al. |
| 2009/0287145 A1 | 11/2009 | Cragg et al. |
| 2009/0319029 A1 | 12/2009 | Evans et al. |
| 2010/0030255 A1 | 2/2010 | Berra et al. |
| 2010/0030321 A1 | 2/2010 | Mach |
| 2010/0036360 A1 | 2/2010 | Herbowy et al. |
| 2010/0049291 A1 | 2/2010 | Yampolsky et al. |
| 2010/0094394 A1 | 4/2010 | Beach et al. |
| 2010/0100167 A1 | 4/2010 | Bortlein et al. |
| 2010/0106239 A1 | 4/2010 | Roeder |
| 2010/0262216 A1 | 10/2010 | Xue |
| 2010/0286756 A1 | 11/2010 | Dorn et al. |
| 2010/0292771 A1 | 11/2010 | Paskar |
| 2010/0305686 A1 | 12/2010 | Cragg et al. |
| 2011/0022149 A1 | 1/2011 | Cox et al. |
| 2011/0125248 A1 | 5/2011 | George et al. |
| 2011/0130819 A1 | 6/2011 | Cragg et al. |
| 2011/0130820 A1 | 6/2011 | Cragg et al. |
| 2011/0130824 A1 | 6/2011 | Cragg et al. |
| 2011/0130825 A1 | 6/2011 | Cragg et al. |
| 2011/0130826 A1 | 6/2011 | Cragg et al. |
| 2011/0178589 A1 | 7/2011 | Andreas et al. |
| 2011/0213450 A1 | 9/2011 | Maclean et al. |
| 2011/0257673 A1 | 10/2011 | Heraty et al. |
| 2011/0264074 A1 | 10/2011 | Tegg et al. |
| 2011/0295354 A1 | 12/2011 | Bueche et al. |
| 2011/0313505 A1 | 12/2011 | McHugo |
| 2012/0041536 A1 | 2/2012 | Hansen |
| 2012/0158115 A9 | 6/2012 | Arnault De La Menardiere et al. |
| 2012/0158117 A1 | 6/2012 | Ryan |
| 2012/0165919 A1 | 6/2012 | Cox et al. |
| 2012/0172968 A1 | 7/2012 | Chuter et al. |
| 2012/0185031 A1 | 7/2012 | Ryan et al. |
| 2012/0197376 A1 | 8/2012 | Heidner et al. |
| 2012/0209063 A1 | 8/2012 | Nishtala et al. |
| 2012/0221091 A1 | 8/2012 | Hartly et al. |
| 2012/0221093 A1 | 8/2012 | McHugo |
| 2012/0330398 A1 | 12/2012 | Hyodoh et al. |
| 2013/0035749 A1 | 2/2013 | Farag |
| 2013/0096407 A1 | 4/2013 | Bednarek et al. |
| 2013/0123898 A1 | 5/2013 | Tung et al. |
| 2013/0131774 A1 | 5/2013 | Nabulsi et al. |

FOREIGN PATENT DOCUMENTS

| | | |
|---|---|---|
| EP | 971646 | 9/2004 |
| EP | 1803418 B1 | 10/2008 |
| WO | WO-9319703 | 10/1993 |
| WO | WO-9632077 A1 | 10/1996 |
| WO | WO-9852496 | 11/1998 |
| WO | WO-9855047 A1 | 12/1998 |
| WO | WO-0105332 A1 | 1/2001 |
| WO | WO-0152770 A1 | 7/2001 |
| WO | WO-03084439 | 10/2003 |
| WO | WO-2005112823 | 12/2005 |
| WO | WO-2009/140638 A1 | 11/2009 |
| WO | WO-2010/132836 A2 | 11/2010 |
| WO | WO-2011068915 | 11/2010 |

(56) References Cited

FOREIGN PATENT DOCUMENTS

| WO | WO-2011003019 A1 | 1/2011 |
|---|---|---|
| WO | WO2012040240 | 3/2012 |
| WO | WO-2012128846 | 9/2012 |

OTHER PUBLICATIONS

Brewster, DC; "Initial Experience with Endovascular Aneurysm Repair: Comparison of Early Results with Outcome of Conventional Open Repair"; J Vasc Surg; Jun. 1998; vol. 27, Issue 6, pp. 992-1003; discussion 1004-5 (14 pages).

Cao, P.; "Comparison of Surveillance vs Aortic Endografting for Small Aneurysm Repair (CAESAR) Trial: Study Design and Progress"; Eur. J. Vasc. Endovasc. Surg.; Sep. 2005; vol. 30, Issue 3; pp. 245-251 (7 pages).

Dorros, G. et al.; "Evaluation of Endovascular Abdominal Aortic Aneurysm Repair: Anatomical Classicication, Procedural Success, Clinical Assessment, and Data Collection"; J. Endovasc Surg; May 1997; vol. 4, Issue 2; pp. 203-225 (24 pages).

Dosluoglu et al.; "Total Percutaneous Endovascular Repair of Abdominal Aortic Aneurysms Using Perclose ProGlide Closure Devices"; J. Endovasc Ther.; Apr. 2007, vol. 14, Issue 2, pp. 184-188 (5 pages).

Faries, PL; "Endovascular Stent Graft Selection for the Treatment of Abdominal Aortic Aneurysms"; J. Cardiovasc Surg (Torino); Feb. 2005; vol. 46, Issue 1, pp. 9-17 (9 pages).

International Search Report and Writton Opinion, PCT/US2011/052412, Mailed on Jan. 17, 2012, Applicant: Altura Medical, Inc., 9 pages.

Mathison, MN; "Implications of Problematic Access in Transluminal Endografting of Abdominal Aortic Aneurysm"; J Vasc Interv Radiol; Jan. 2003; vol. 14, Issue 1, pp. 33-39 (7 pages).

Matsumura, JS; "A Multicenter Controlled Clinical Trial of Open Versus Endovascular Treatment of Abdominal Aortic Aneurysm"; J Vasc Surg; Feb. 2003; vol. 37, Issue 2, pp. 262-271 (13 pages).

Non-Final Office Action, U.S. Appl. No. 12/466,044, dated May 7, 2012, 35 pages.

Non-Final Office Action, U.S. Appl. No. 12/628,131, dated May 11, 2012, 35 pages.

Parodi, J.C. et al., "Transfemoral Intraluminal Graft Implantation for Abdominal Aortic Aneurysms", Ann Vasc Surg.; Nov. 1991; vol. 5, Issue 6, pp. 491-499 (9 pages).

Powell, J.T. et al.; "Final 12-year Follow-up of Surgery Versus Surveillance in the UK Small Aneurysm Trial"; Br. J. Surg.; Jun. 2007; vol. 94, Issue 6, pp. 702-708 (7 pages).

Volodos, N.L. et al.; "Clinical Experience of the use of Self-Fixing Synthetic Prostheses for Remote Endoprosthetics of the Thoracic and the Abdominal Aorta and Iliac Arteries Through the Femoral Artery and as Intraoperative Endoprosthesis for Aorta Reconstruction"; Kharkov Research Institute of General and urgent Surgery; J. Vasa Diseases-Suppl.; 1991; vol. 33, pp. 93-95 (5 pages).

Zarins, C.K.; "AneuRx Stent Graft Versus Open Surgical Repair of Abdominal Aortic Aneurysms: Multicenter Prospective Clinical Trial"; J Vasc Surg; Feb. 1999; vol. 29, Issue 2, pp. 292-308 (19 pages).

Zarins C.K.; "Endovascular Repair or Surveillance of Patients with Small AAA"; Eur. J. Vasc. Endovasc. Surg.; May 2005; vol. 29, Issue 5; pp. 496-503; located at www.sciencedirect.com (9 pages).

U.S. Appl. No. 61/293,581, filed Jan. 8, 2010, Cragg et al.
U.S. Appl. No. 61/311,735, filed Mar. 8, 2010, Cragg et al.
U.S. Appl. No. 61/320,646, filed Apr. 2, 2010, Cragg et al.
U.S. Appl. No. 61/384,669, filed Sep. 20, 2010, Cragg et al.
U.S. Appl. No. 61/053,378, filed May 15, 2008, Cragg et al.
U.S. Appl. No. 61/265,713, filed Dec. 1, 2009, Cragg et al.

International Search Report and Written Opinion, PCT/US09/44212, Mailed on Jul. 14, 2009, Applicant: Altura Medical, Inc., 11 pages.

International Search Report and Written Opinion, PCT/US10/58621, Mailed on Feb. 9, 2011, Applicant: Altura Medical, Inc., 34 pages.

International Search Report and Written Opinion, PCT/US2010/035003, Mailed on Feb. 9, 2011, Applicant: Altura Medical, Inc., 10 pages.

Laborde, Jean Claude et al., "A Novel 14F Endograft for Abdominal Aortic Aneurysm: First in Man," *Catheterization and Cardiovascular Interventions*, Jun. 2010 (20 pages).

U.S. Appl. No. 13/963,912, filed Aug. 9, 2013, Cragg et al.
U.S. Appl. No. 13/964,013, filed Aug. 9, 2013, Cragg et al.

Dereume, J.P. et al., "Endoluminal Treatment of Abdominal Aortic Aneurysm with the Corvita Endovascular Graft. Results of a Single-Center, Prospective Feasibility Study of 90 Patients," Journal of Endovascular Surgery; Nov. 1996, vol. 3, 1 page.

Sanchez, Luis et al., "Early Experience with the Corvita Endoluminal Graft for Treatment of Arterial Injuries," from the Divisions of Vascular Surgery and Interventional Radiology, Montefiore Medical Center, New York. Presented May 31, 1997, 7 pages.

Sitsen, M. et al al., "Deformation of Self-Expanding Stent-Grafts Complicating Endovascular Peripheral Aneurysm Repair," J Endovascular Surgery, 1999, 5 pages.

Chinese Preliminary Examination Report; Chinese Patent Application No. 100876, mailed Mar. 30, 2012, 1 page Non-Final Office Action; U.S. Appl. No. 13/237,822, mailed Dec. 5, 2013, 11 pages.

Australian Preliminary Patent Examination Report No. 1; Australian Patent Application No. 2012203707, dated Jan. 31, 2013, 4 pages.

Final Office Action; U.S. Appl. No. 12/466,044; dated Sep. 14, 2012; 9 pages.

Final Office Action; U.S. Appl. No. 12/628,131; dated Nov. 21, 2012; 19 pages.

Final Office Action; U.S. Appl. No. 12/958,381; dated Jan. 31, 2013; 36 pages.

Final Office Action; U.S. Appl. No. 12/958,383; dated Jan. 9, 2013; 29 pages.

Kahraman, H. et al., "The Diameters of the Aorta and Its Major Branches in Patients with Isolated Coronary Artery Ectasia," Texas Heart Institute Journal; 2006, vol. 33, No. 4, pp. 463-468.

Non-Final Office Action, U.S. Appl. No. 12/958,367, dated Aug. 17, 2012, 28 pages.

Non-Final Office Action, U.S. Appl. No. 12/958,374, dated Aug. 16, 2012, 28 pages.

Non-Final Office Action, U.S. Appl. No. 12/958,378, dated Aug. 16, 2012, 25 pages.

Non-Final Office Action, U.S. Appl. No. 12/958,381, dated Aug. 9, 2012, 30 pages.

Non-Final Office Action, U.S. Appl. No. 12/958,383, dated Aug. 16, 2012, 28 pages.

Non-Final Office Action, U.S. Appl. No. 12/466,044, dated Jan. 3, 2013, 12 pages.

\* cited by examiner

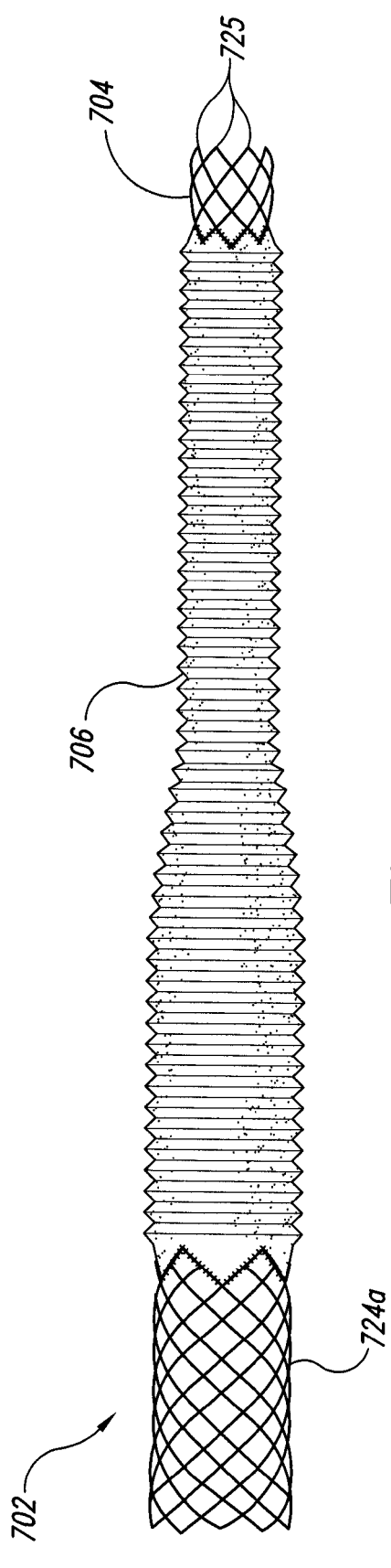
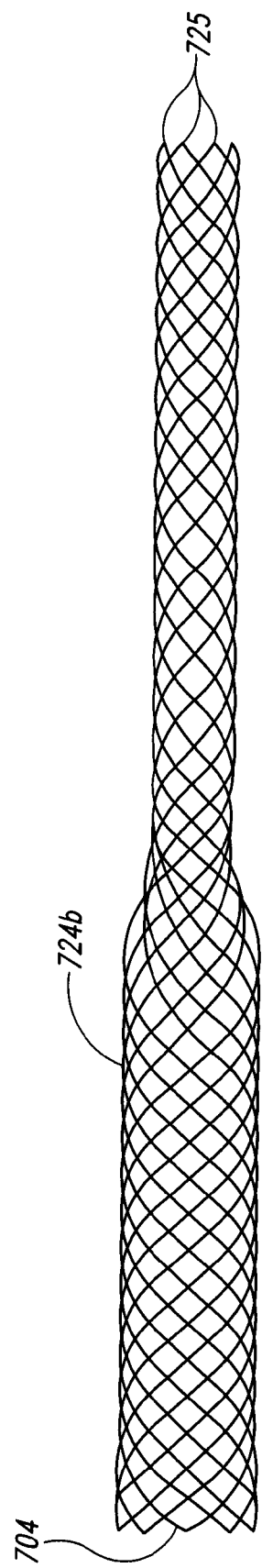
Fig. 7A
Fig. 7B

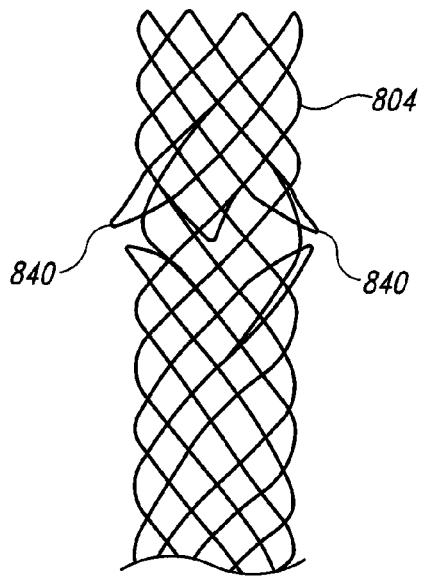
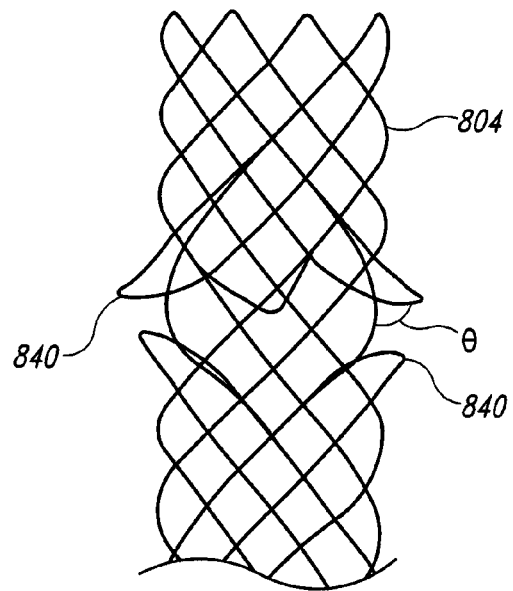
Fig. 8    Fig. 9
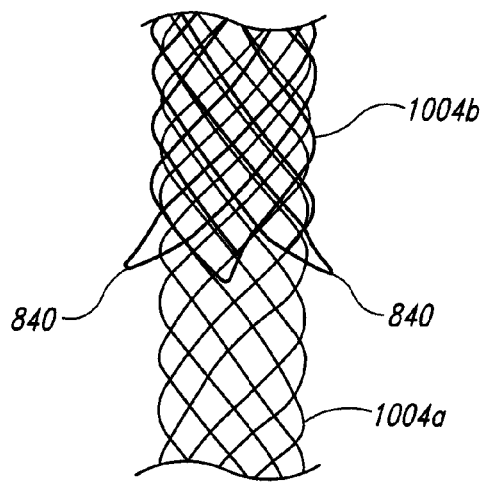
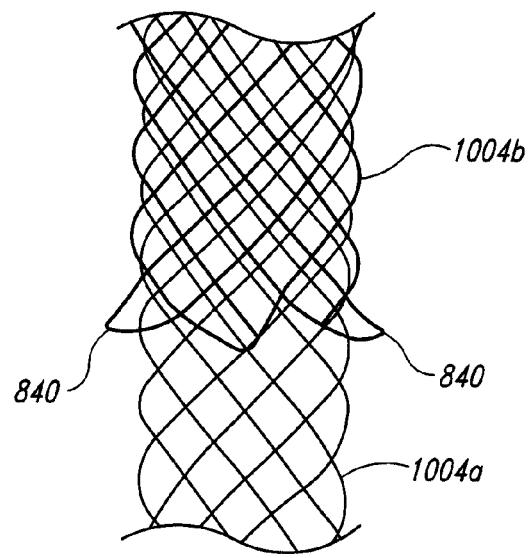
Fig. 10    Fig. 11

STENT GRAFT DELIVERY SYSTEMS AND ASSOCIATED METHODS

CROSS-REFERENCE TO RELATED APPLICATIONS

This application claims priority to and the benefit of U.S. Provisional Patent Application No. 61/384,669, filed Sep. 20, 2010, entitled "STENT GRAFT DELIVERY SYSTEMS AND METHODS," and U.S. Provisional Patent Application No. 61/527,064, filed Aug. 24, 2011, entitled "ENDOVASCULAR STENT GRAFT DELIVERY SYSTEMS AND ASSOCIATED METHODS," both of which are incorporated herein by reference in their entireties.

The following patent applications are also incorporated by reference herein in their entireties:

(a) U.S. patent application Ser. No. 12/466,044, filed May 14, 2009;
(b) U.S. patent application Ser. No. 12/628,131, filed Nov. 30, 2009;
(c) U.S. Provisional Pat. App. No. 61/265,713, filed Dec. 1, 2009;
(d) U.S. Provisional Pat. App. No. 61/293,581, filed Jan. 11, 2010; and
(e) U.S. Provisional Pat. App. No. 61/320,646, filed Apr. 2, 2010.

TECHNICAL FIELD

The present technology relates to treatment of abdominal aortic aneurysms. More particularly, the present technology relates to stent graft delivery systems and associated methods.

BACKGROUND

An aneurysm is a dilation of a blood vessel of at least 1.5 times above its normal diameter. A dilated vessel forms a bulge known as an aneurysmal sac that can weaken vessel walls and eventually rupture. Aneurysms are most common in the arteries at the base of the brain (i.e., the Circle of Willis) and in the largest artery in the human body, the aorta. The abdominal aorta, spanning from the diaphragm to the aortoiliac bifurcation, is the most common site for aortic aneurysms. Such abdominal aortic aneurysms (AAAs) typically occur between the renal and iliac arteries, and are presently one of the leading causes of death in the United States.

The two primary treatments for AAAs are open surgical repair and endovascular aneurysm repair (EVAR). Surgical repair typically includes opening the dilated portion of the aorta, inserting a synthetic tube, and closing the aneurysmal sac around the tube. Such AAA surgical repairs are highly invasive, and are therefore associated with significant levels of morbidity and operative mortality. In addition, surgical repair is not a viable option for many patients due to their physical conditions.

Minimally invasive endovascular aneurysm repair (EVAR) treatments that implant stent grafts across aneurysmal regions of the aorta have been developed as an alternative or improvement to open surgery. EVAR typically includes inserting a delivery catheter into the femoral artery, guiding the catheter to the site of the aneurysm via X-ray visualization, and delivering a synthetic stent graft to the AAA via the catheter. The stent graft reinforces the weakened section of the aorta to prevent rupture of the aneurysm, and directs the flow of blood through the stent graft away from the aneurismal region. Accordingly, the stent graft causes blood flow to bypass the aneurysm and allows the aneurysm to shrink over time.

Conventional stent grafts are made from surgical grade materials that are inherently thick and rigid, and therefore associated delivery systems typically have a size of approximately 20 Fr (i.e., approximately 6.7 mm in diameter) and greater. This size can be intrusive when placed through small iliac vessels, and accordingly cut-down procedures are used to introduce the delivery catheter. Cut-down procedures result in longer and more uncomfortable healing processes than if the stent graft was implanted using a smaller, percutaneously deliverable system. However, reducing the diameter of the delivery catheter (e.g., to allow for percutaneous implantation) increases the force required to unsheathe and expose the stent graft. This increased force also reduces control and precision during deployment, making it more difficult for a physician to implant the stent graft and potentially causing damage to the stent graft and/or the surrounding vessel walls.

BRIEF DESCRIPTION OF THE DRAWINGS

FIGS. 7A and 7B are side views of a stent graft and a stent frame, respectively, configured in accordance with embodiments of the present technology.

FIGS. 8 and 9 are enlarged views of a superior portion of a stent frame having medial turns configured in accordance with an embodiment of the present technology.

FIGS. 10 and 11 are partial side views of two stent frames interlocked by medial turns in accordance with another embodiment of the present technology.

DETAILED DESCRIPTION

The present technology is directed toward stent graft delivery systems and associated methods. In several embodiments, for example, a stent graft delivery system includes proximal and distal catheters that can be individually manipulated to deploy a stent graft. In further embodiments, stent graft delivery systems configured in accordance with the present technology can include a stent cover that houses at least a portion of a stent graft prior to and during delivery of the stent graft to the aneurysm. The stent cover maintains the low profile of the stent graft such that the stent graft can fit into smaller sized delivery introducers (e.g., 14 Fr, 12 Fr, 10 Fr introducers), and also provides low stent deployment forces that enable control and precision during deployment.

Certain specific details are set forth in the following description and in FIGS. 1A-18 to provide a thorough understanding of various embodiments of the technology. For example, many embodiments are described below with respect to the delivery of stent grafts that at least partially repair AAAs. In other applications and other embodiments, however, the technology can be used to repair aneurysms in other portions of the vasculature. Other details describing well-known structures and systems often associated with stent grafts and associated delivery devices and procedures have not been set forth in the following disclosure to avoid unnecessarily obscuring the description of the various embodiments of the technology. A person of ordinary skill in the art, therefore, will accordingly understand that the technology may have other embodiments with additional elements, or the technology may have other embodiments without several of the features shown and described below with reference to FIGS. 1A-18.

In this application, the terms "distal" and "proximal" can reference a relative position of the portions of an implantable stent graft device and/or a delivery device with reference to an operator. Proximal refers to a position closer to the operator of the device, and distal refers to a position that is more distant from the operator of the device.

Selected Stent Graft Structures

Figure 1A:
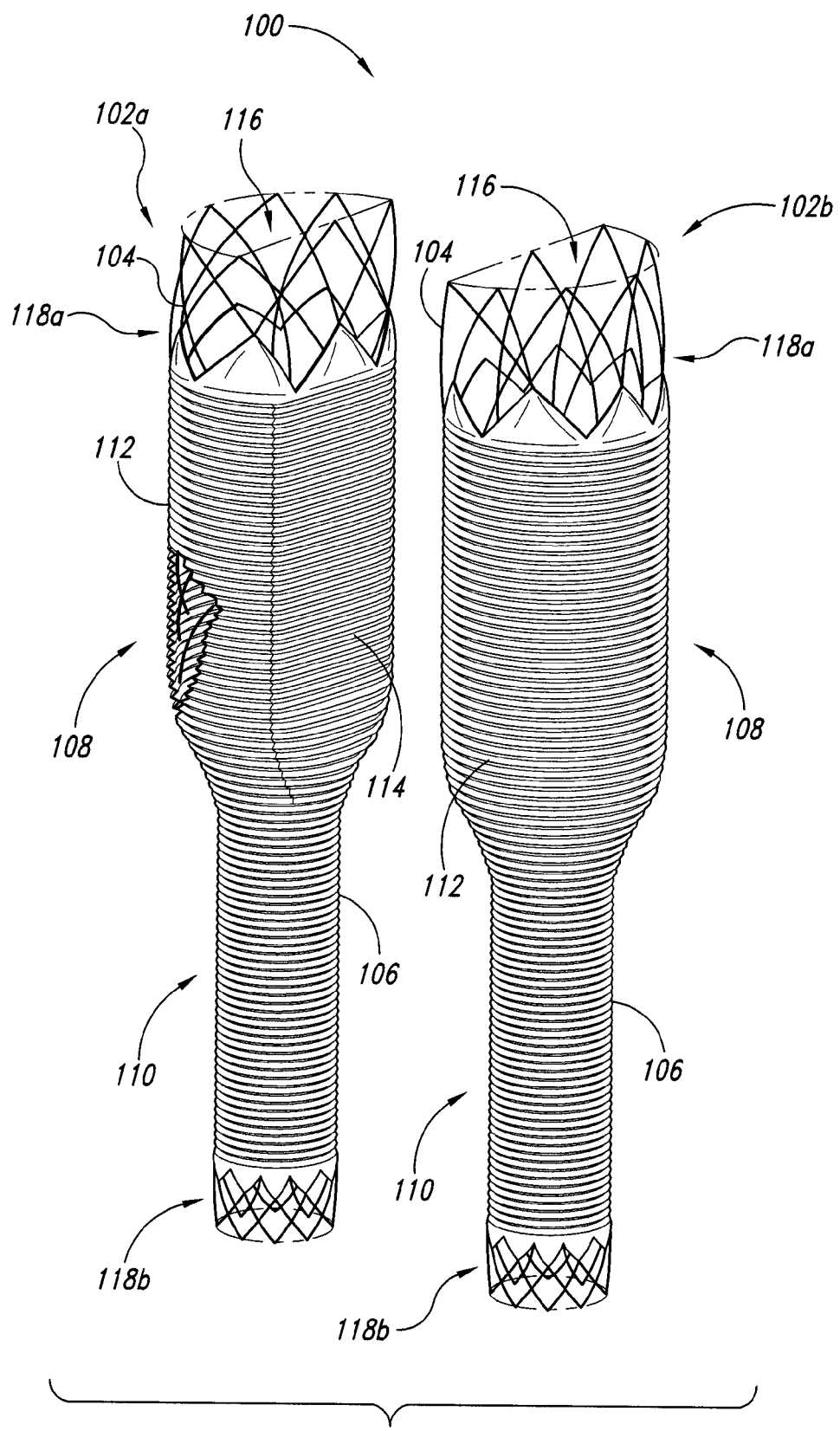
FIG. 1A is a partial cut-away, isometric view of a modular stent graft system configured in accordance with an embodiment of the present technology.
Figure 1B:
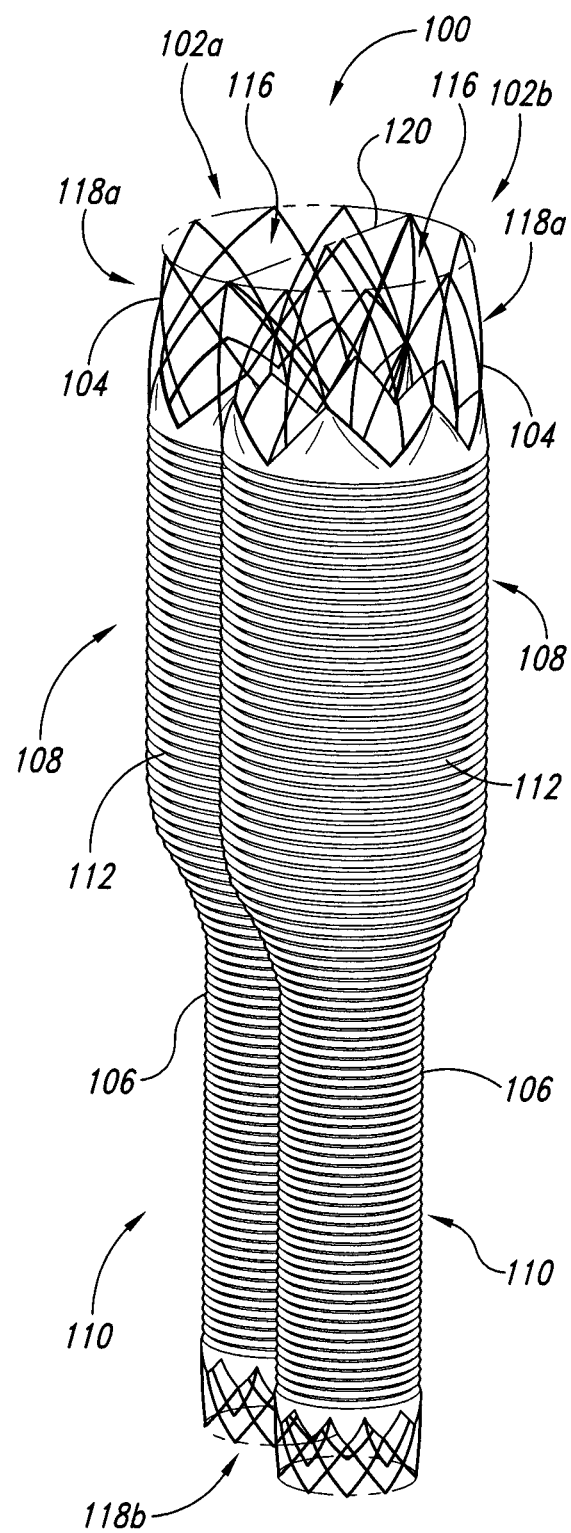
FIG. 1B is an isometric view of the modular stent graft system of FIG. 1A in a sealed configuration in accordance with an embodiment of the present technology.

FIGS. 1A and 1B are isometric views of a modular stent graft system 100 ("system 100") configured in accordance with an embodiment of the present technology. The system 100 can include separate stent grafts 102 (identified individually as a first stent graft 102a and a second stent graft 102b) that can be coupled, mated, or otherwise substantially sealed together in situ. Each stent graft 102, for example, can include a braided or integrated frame 104 ("frame 104") and an at least substantially impermeable sleeve or cover 106 ("cover 106") extending over at least a portion of the frame 104. The frame 104 and the cover 106 of an individual stent graft 102 can form a discrete lumen 116 through which blood can flow to bypass an aneurysm. In operation, the stent grafts 102 are generally delivered separately and positioned independently across the aneurysm.

As shown in FIGS. 1A and 1B, each stent graft 102 includes a superior portion 108 and an inferior portion 110. The superior portion 108 can include a convexly curved outer wall 112 and a septal wall 114. As shown in FIG. 1A, the septal wall 114 can be substantially flat such that the superior portion 108 forms a "D" shape at a superior portion of the lumen 116. In other embodiments, the septal wall 114 can be convexly curved with a larger radius of curvature than the outer wall 112 such that the superior portion 108 forms a complex ellipsoid having another D-shaped cross-section at the superior portion of the lumen 116. In further embodiments, the superior portion 108 can have asymmetrical shapes or other suitable cross-sectional configurations that can mate with each other in the septal region and mate with an arterial wall around the periphery of the outer wall 112. The inferior portion 110 can have a circular cross-sectional shape, an elliptical shape, a rectangular shape, an asymmetrical shape, and/or another suitable cross-sectional shape for an inferior portion of the lumen 116.

The superior portions 108 of the stent grafts 102 are mated together and at least substantially sealed along the septal walls 114 (e.g., as shown in FIG. 1B) within the aorta above an aneurysm. In some embodiments, the superior portion 108 can be approximately 2-4 cm in length to adequately fix the outer walls 112 to the arterial walls such that they are at least substantially sealed together. In other embodiments, the superior portion 108 can be longer or shorter. In one embodiment in accordance with the technology, the inferior portions 110 can extend through an inferior portion of the aneurysm and into corresponding iliac arteries to bypass the aneurysm. In another embodiment, one or both inferior portions 110 can terminate within the aneurysm to form what is known to those skilled in the art as a "gate," and limbs (not shown) can be attached to the proximal ends of the inferior portions 110 and extended into the iliac arteries to bypass the aneurysm.

In the embodiment shown in FIGS. 1A and 1B, the frames 104 have bare end portions 118 (identified individually as first end portions 118a and second end portions 118b) that extend beyond the covers 106. As shown in FIGS. 1A and 1B, the first end portion 118a can extend distally from the superior terminus of the cover 106, and the second end portion 118b can extend proximally from the inferior terminus of the cover 106. In some embodiments, the end portions 118 can be trumpeted or flared to interface with the arterial walls of the aorta and/or the iliac arteries. This can promote cell ingrowth that strengthens the seal between the endograft devices 102 and the adjacent arteries.

The end portions 118 can also increase the available structure for securing the stent graft 102 to the artery and increase the surface area of the covers 106 for sealably fixing the stent grafts 102 to arterial walls. This decreases the precision necessary to position the stent grafts 102 and increases the reliability of the implanted system 100. For example, a short infrarenal aortic neck (e.g., less than 2 cm) generally requires precise placement of the stent grafts 102 to preserve blood flow to the renal arteries while still providing enough surface area for the stent grafts 102 to be properly affixed with the aorta. In the embodiment shown in FIGS. 1A and 1B, however, the first end portions 118a can be placed at the entrance of the renal arteries to allow lateral blood flow into the renal arteries and provide a larger structure for fixing the stent grafts 102 to the arterial wall and a larger sealing area with the arterial wall. The end portions 118 can also provide accessible sites for recapture (e.g., by guidewires, bead and collet, etc.) that enhance the accuracy of positioning the stent grafts 102 across the aneurysm.

During deployment of the system 100, each stent graft 102 can be delivered independently to an aneurysmal region in a low-profile configuration. The low-profile configuration has a first cross-sectional dimension and a first length that can facilitate percutaneous endovascular delivery of the system 100. Because each stent graft 102 extends around only a portion of the vessel periphery, the individual stent grafts 102 can be constricted (i.e., radially collapsed) to a smaller diameter than conventional AAA stent grafts with a single superior portion that extends around the complete periphery of the vessel wall. In some embodiments, for example, each of the stent grafts 102 can have a diameter of 25 mm in the expanded configuration, and can be constricted to a diameter of 4 mm in the low-profile configuration to be percutaneously deployed across the aneurysm through a 12 Fr catheter. Additionally, because each stent graft 102 can be delivered independently, the end portions 118 and fenestrations can facilitate staggering the stent grafts 102 to accommodate asymmetrical anatomies.

At a target site in the aneurysmal region, the stent grafts 102 can expand (e.g., manually or self-expand) to an expanded configuration (e.g., shown in FIGS. 1A and 1B). The expanded configuration can have a second cross-sectional dimension greater than the first cross-sectional dimension and a second length less than the first length. In the expanded configuration shown in FIG. 1B, the septal walls 114 (FIG. 1A) of the stent grafts 102 can be forced against one another. When in situ within the aorta, the forces between the opposing septal walls 114 form a septum 120 in which the septal walls 114 are at least substantially sealed together to prevent blood from flowing between the stent grafts 102 and into the aneurysm. Additionally, as shown in FIG. 1B, the texture (e.g., ribbing) on the covers 106 can mate at the septum 120 to further strengthen the seal between the septal walls 114. Similarly, the texture of the cover 106 on the outer walls 112 can interface with the adjacent vessel walls to strengthen the seal around the periphery of the stent grafts 102.

In other embodiments, a single stent graft can be used to direct blood flow away from a diseased aneurismal portion of a blood vessel through the stent graft. Such a stent graft can includes features generally similar to the features of the stent grafts 102 of the dual stent graft system 100 described above with reference to FIGS. 1A and 1B. For example, the single stent graft can include the intergrated frame 104 and the ribbed cover 106 that expand radially from a low-profile configuration used during delivery to an expanded configuration at the site of the aneurysm. In this embodiment, however, the superior portion of the stent graft can have a substantially circular cross-sectional shape to seal against the circumference of the aorta.

Figure 2:
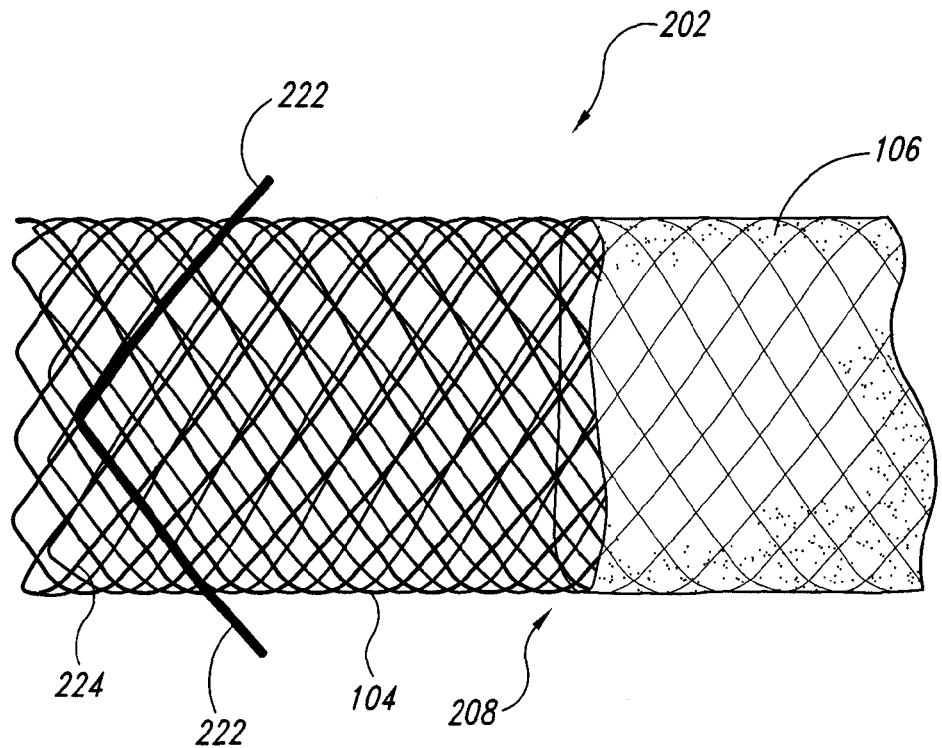
FIG. 2 is an enlarged view of a superior portion of a stent graft having anchoring barbs configured in accordance with an embodiment of the present technology.

FIG. 2 is an enlarged isometric view of a superior portion 208 of a stent graft 202 configured in accordance with another embodiment of the present technology. The stent graft 202 includes features generally similar to the features of the stent grafts 102 described above with reference to FIGS. 1A and 1B. For example, the stent graft 202 includes the integrated frame 104 and the cover 106. The stent graft 202 can be one of a pair of D-shaped stent grafts as described above or a circular stent graft.

As shown in FIG. 2, the stent graft 202 further includes one or more anchoring barbs 222 that project radially outward from the frame 104 to engage the interior surfaces of arterial walls. The anchoring barbs 222 can be "V" shaped projections as shown, hooks, and/or other shapes that can penetrate into the arterial walls to resist migration of the stent graft 202 within the artery and reduce the likelihood of endoleaks between the outer wall of the stent graft 202 and the arterial wall. The anchoring barbs 222 can be made from resilient metallic materials, polymeric materials (e.g., polyethylenes, polypropylenes, Nylons, PTFEs), and/or other suitable materials that can anchor the stent graft 202 to arterial walls. In the illustrated embodiment, the stent graft 202 includes two anchoring barbs 222. In other embodiments, however, the stent graft 202 can include one anchoring barb 222 or more than two anchoring barb 222 positioned on the superior and/or inferior portions of the stent graft 202

In various embodiments, the anchoring barbs 222 can be separate elements that are attached to the frame 104. For example, the anchoring barbs 222 can be small wires that are fastened to the frame 104 by winding another wire (e.g., a Nitinol wire) around the anchoring barbs 222 and an adjacent wire 224 of the frame 104. In other embodiments, the anchoring barbs are integrally formed with the wires 224 used in the braid of the frame 104. Such integrated anchoring barbs 222 can deploy (i.e., project outwardly) and retract in a manner responsive to at least one of elongation, shortening, contraction, and dilation of the frame 104. For example, the anchoring barbs 222 can be deployed when the frame 104 expands and can retract when the frame 104 constricts. Accordingly, the anchoring barbs 222 do not inhibit movement of the stent graft 202 during delivery in the low-profile configuration.

Stent Graft Delivery Systems

Figure 3:
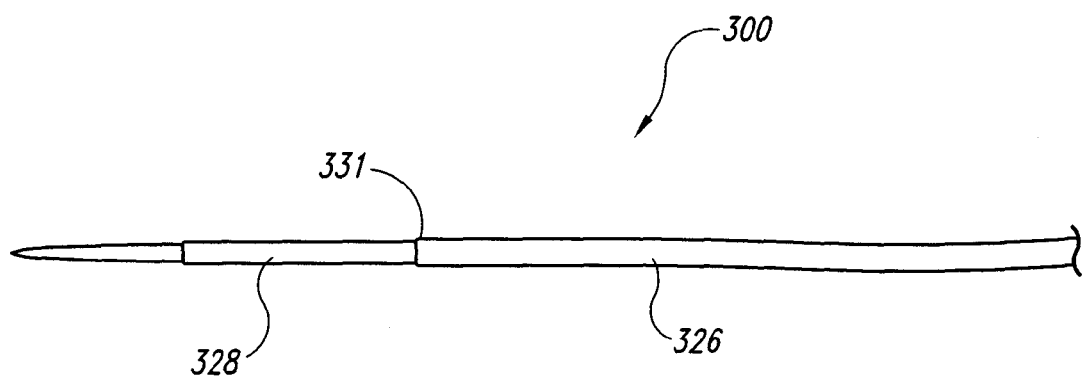
FIGS. 3-6 illustrate various stages of deploying a stent graft from a delivery system configured in accordance with an embodiment of the present technology.
Figure 4:
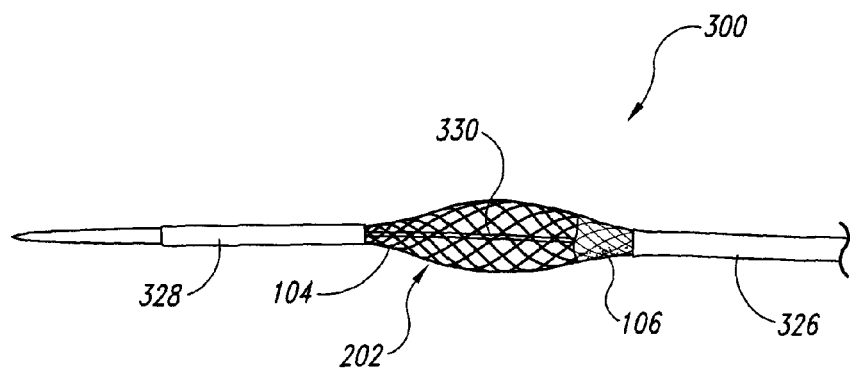
Figure 5:
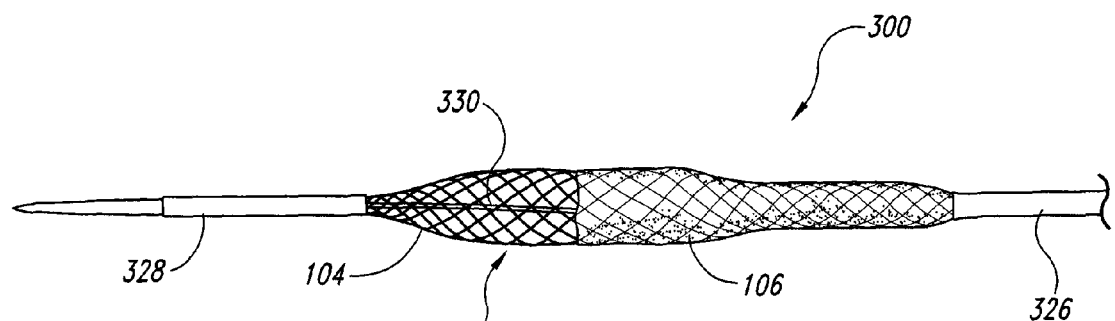

FIGS. 3-6 are top views a delivery system 300 in various stages of deploying a stent graft and configured in accordance with an embodiment of the present technology. In the illustrated embodiment, the delivery system 300 is shown deploying the stent graft 202 of FIG. 2. However, the delivery system 300 may be used to deliver any suitable stent graft. Referring to FIG. 3, the delivery system 300 can include a proximal sheath 326 that covers a proximal portion of the stent graft 202 (not shown) and a distal sheath 328 that covers a distal portion of the stent frame 202. The proximal sheath 326 and the distal sheath 328 may cover contiguous portions of the stent frame, leave a medial portion uncovered, and/or overlap to fully cover the stent graft 202. In other embodiments, the delivery system 300 can include more than two delivery sheaths, each configured to cover at least a portion of a stent graft In operation, the delivery system 300 is can deliver the stent graft 202 to a deployment location in the vasculature of a patient. For example, the delivery system 300 may be delivered percutaneously into a vessel (e.g., inserted in the femoral artery) and guided to the site of an abdominal aortic aneurysm. As shown in FIGS. 4 and 5, upon arrival at the deployment location, the proximal sheath 326 can be retracted relative to the stent graft 202 and relative to the distal sheath 328, thereby uncovering and deploying at least a proximal portion of the stent graft 202.

As shown in FIGS. 4 and 5, in various embodiments, the distal sheath 328 may continue to cover the distal portion of the stent graft 202 while the proximal sheath 326 is retracted. For example, the distal sheath 328 may cover a portion of the stent graft 202 including the anchoring barbs 222 (FIG. 6) while other portions of the stent graft 202 are deployed. This allows the anchoring barbs 222 to remain unanchored to the surrounding tissue (e.g., the arterial walls) during deployment of other portions of the stent graft 202 not including anchoring barbs 222 such that the anchoring barbs 222 do not injure the surrounding tissue during lateral or longitudinal adjustments to the position of the stent graft 202.

Figure 6:
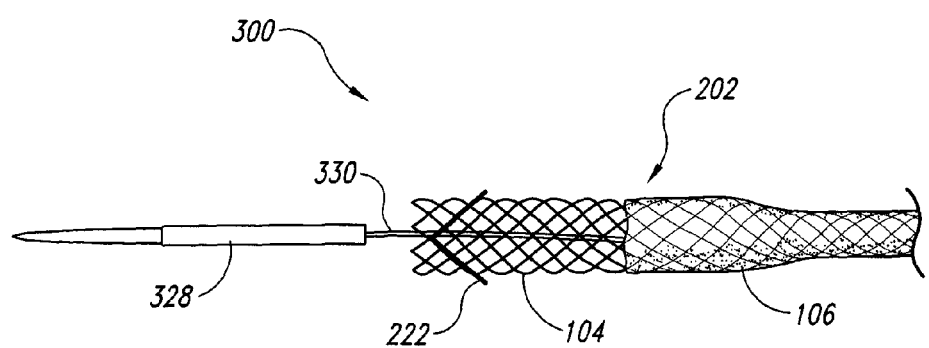

As shown in FIG. 6, once the stent graft 202 is positioned in the desired location, the distal sheath 328 can be advanced relative to the stent graft 202 to deploy the distal portion of the stent graft 202 and the anchoring barbs 222 attached thereto. In the illustrated embodiment, the distal sheath 328 is operable by a user via a central wire 330 (e.g., as shown in FIGS. 3, 4, and 5). The central wire 330 can be made from a material that is flexible enough to navigate tortuous anatomy (e.g., the iliac arteries and/or other portions of the vasculature), but still stiff enough to translate advancement thereof by a user to the distal sheath 328, such as stainless steel, Nitinol, and/or other suitable materials. To navigate the vasculature, the central wire 330 can be positioned through the lumen formed at least in part by the proximal sheath 326 and the stent graft 202. Once the distal portion of the stent graft 202 is deployed, the central wire 330 can be used to remove the distal sheath 328 and any other distal portions of the delivery system 300 through the central lumen of the stent graft 202.

In various aspects of the present technology, the delivery system 300 may be used to deploy the stent graft 202 and/or other stent grafts using various other methods. For example, in one embodiment, a distal portion of a stent graft can be deployed before a proximal portion of the stent frame. As another example, one of the sheaths (e.g., the distal sheath 328 or the proximal sheath 326) can be only partially removed from a stent graft before adjusting the other sheath. In further embodiments, the delivery system 300 can include additional sheaths to further provide controllable deployment of portions of a stent graft.

In further aspects of the present technology, the delivery system 300 can include features that enhance expansion and/or constriction of stent grafts (e.g., to achieve full expansion of the two D-shaped stent grafts 102 of FIGS. 1A and 1B). For example, the delivery system 300 may include spur-shaped elements on telescoping coaxial tubes to engage portions (e.g., proximal and/or distal portions) of a stent graft while it is constrained within one or both of the sheaths 326 and 328. Engaging portions of the stent graft can provide axial control at one or more points along the stent graft. For example, the delivery system 300 can engage an aortic or distal end portion of a stent graft (i.e., the portion of the stent graft eventually deployed within the aorta) to stabilize it, while another portion of the delivery system 300 engages an iliac or proximal end portion of the stent graft to move it proximally and constrain or constrict the stent graft 202 as it is exposed from the sheaths 326 and 328. This coordinated motion can be used to achieve a controlled braid angle of the frame as the stent graft is exposed. By grasping the distal and/or proximal end portions of the stent graft, the delivery system 300 can also maintain the position of a stent graft relative to the deployment location (e.g., an AAA). In other embodiments, the delivery system 300 can include engagement features that connect to other portions of the stent graft.

In still further aspects of the present technology, the deployment system 300 can be used to deliver an expandable stent graft, such as the expandable stent grafts 102 and 202 discussed above with reference to FIGS. 1A-2. For example, one or more sheaths (e.g., the proximal sheath 326 and/or the distal sheath 328) can cover the stent graft during delivery such that it is in a low-profile, sheathed configuration with an elongated length, and during deployment the stent graft can be unsheathed such that it expands and shortens in length to a deployed configuration. The sheath may be removed from the proximal or distal end of the stent graft as described above.

In yet another aspect of the present technology, the delivery system 300 includes a gear arrangement 331 (FIG. 3) between or connecting one or more sheaths (e.g., the proximal sheath 326, the distal sheath 328) to a stent graft positioned therein. The gear arrangement 331 may be configured to advance the stent graft while simultaneously retracting the sheath relative to the stent graft such that an end portion (e.g., a proximal end portion or a distal end portion) of the stent graft is held in a position (e.g., at a desired location relative to the aneurysm) while the sheath is removed and the stent graft transitions from the sheathed configuration to the deployed configuration. In other embodiments, the gear arrangement 331 may be configured to retract the stent graft (e.g., rather than the sheath) while simultaneously advancing the sheath relative to the stent graft such that one of the proximal or distal end portions of the stent graft is held in place while transitioning the stent graft from the sheathed configuration to the deployed configuration.

When the stent graft includes anchoring barbs (e.g., the stent graft 202 of FIG. 2 with anchoring barbs 222), the portion of the stent graft that includes the anchoring barbs can be maintained at a single position while the stent graft transitions from the sheathed configuration to the deployed configuration. When the anchoring barbs are deployed before or during stent graft deployment, holding the stent graft in such a fixed location reduces, mitigates, or eliminates damage to the arterial walls caused by the anchoring barbs during deployment of the remainder of the stent graft (e.g., distally directed force as the sheath is removed from the stent graft).

In various embodiments, the gear arrangement 331 can have a gear ratio configured to correspond to a ratio of the shortened length of the stent graft to the elongated length of the stent graft (i.e., the length of the stent graft in the sheathed configuration versus the deployed configuration). This allows the gear arrangement 331 to compensate for foreshortening of the stent graft during deployment. In other embodiments, the gear arrangement 331 may have a gear ratio corresponding to a ratio of the shortened length to the elongated length as it relates to the amount of the stent graft that is being deployed (e.g., when the amount is less than all of the stent frame).

Selected Embodiments of Stent Frames and Covers

FIGS. 7A and 7B are side views of a stent graft 702 and a stent frame 704, respectively, configured in accordance with embodiments of the present technology. The stent graft 702 and stent frame 704 can include features generally similar to the features of the stent grafts 102 and 202 described above with reference to FIGS. 1A-2. Referring to FIG. 7B, the frame 704 can have a braided structure made from one or more continuous interwoven wires 724 that provide continuous integrated support longitudinally along the length of the frame 704. For example, a single wire 724 can be interwoven to form a braid pattern and looped at the end portions of the frame 704 to form turns 725 (e.g., by looping the wire partially around a pin or other structure) and reverse direction to continue weaving along the length of the frame 704 toward the opposite end portion. In various embodiments, the intersections of the wire 724 are not welded or otherwise fixed together such that they remain unbound. As such, each area of the frame 704 influences the radial expansion or contraction of an adjacent area of the frame 704. In further embodiments, the frame 704 can be configured such that the wires 724 do not terminate at the end portions of the braid structure (i.e., at the turns 725) where stress concentration may be highest. Instead, the ends of each wire 724 in the braid structure can overlap an opposing end of the same wire or an adjacent wire along the length of the braid structure, can be crimped in suitable splice tube, and/or otherwise affixed to a medial portion of the braid structure.

Braid structures can include variations in the number of turns 725 (e.g., loops in the wires 724 at the ends of the braid structure), in the thicknesses of the wires 724, and in the geometries of the braid (e.g., different braid angles). The frame 704 shown in FIG. 7A, for example, is made from a wire 724a having a thickness of approximately 0.013 inch that forms 10 turns 725 at each end portion of the frame 704. The frame 704 shown in FIG. 7B includes a wire 724b having a thickness of approximately 0.012 inch that forms 8 turns 725 at each end portion of the frame 704.

The frame 704 may be constructed from a variety of resilient metallic materials, polymeric materials (e.g., polyethylenes, polypropylenes, Nylons, PTFEs, and the like), and composites of materials. For example, the wires 724 can be made from biocompatible stainless steels, highly elastic metallic alloys, and biocompatible shape setting materials (e.g., Nitinol) that exhibit shape memory properties.

In various embodiments, the frame 704 can be constrained (e.g., elongated and contracted) to fit within a small sheath of a delivery system (e.g., the proximal sheath 326 and/or the distal sheath 328 of the delivery system 300 of FIGS. 3-6). To facilitate maximal constriction of the frame 704, each longitudinal segment of the braided wire 724 (e.g., between opposing turns 725) can have a substantially equal length. When the frame 704 has varying cross-sectional dimensions or shapes (e.g., a D-shaped superior portion and a circular inferior portion as shown in FIGS. 1A and 1B), the frame 704 can be formed in two stages: (1) the wire 724 can be braided on a dual-diameter mandrel, and (2) a portion of the braided wire 724 can be reshaped on a D-shaped mandrel. This allows the wire 724 to maintain uniform end-to-end distances while conforming to the D-shaped cross section.

In various embodiments, the braid pattern of the stent frames 704 can be interrupted to create V-shaped wire turnarounds or medial turns along the length of the braid structure (e.g., midway through the length of the braid structure). Such medial turns can be included in a braid structure that includes multiple wires. For example, in one embodiment, a wire is braided into a first braid pattern (e.g., defining a body of the frame 704) having half of the desired braid density and half of the desired turns at each end portion. A second wire is then braided into the first braid pattern with a set of turnarounds near an end portion of the first braid pattern and a second set of turnarounds between the two end portions (e.g., toward the middle) of the first braid pattern. A third wire can then be braided into the remaining portion of the first braided structure (i.e., the portion of the first braid pattern not already integrated with the second braid pattern) with medial turns proximate the medial turns of the second wire to "fill in" the frame, making the wire density is more uniform along the length of the frame. The apex of individual medial turns may point generally toward one end of the stent frame such that they are flush with the body of the frame.

FIGS. 8 and 9 are enlarged views of a distal portion of a stent frame 804 configured in accordance with another embodiment of the present technology. The stent frames 804 include features generally similar to the features of the frames discussed above. However, as shown in FIGS. 8 and 9, the stent frames 804 include medial turns 840 that are bent or otherwise formed to extend or flare radially outward away from the center lumen of the stent frame 804 beyond what would otherwise be defined as the body of the stent frame 804. As discussed in more detail below, the angle θ at which the medial turns 840 project relative to the body of the stent frame 804 may be defined according to desired attributes.

In operation, the medial turns 840 can provide a hook or other type of engagement feature that catches on wire diamonds formed by the braid pattern of another stent frame. For example, FIGS. 10 and 11 are side views of a first stent frame 1004a having medial turns 840 that are disposed substantially concentrically within a second braided stent frame 1004b. The first stent frame 1004a can be expanded within the second stent frame 1004b such that the medial turns extend through the openings of the second stent frame 1004b. This resists rotation and axial movement of the two stent frames 1004 with respect to one another. In various embodiments, the medial turns 804 are angled away from the body of the first stent frame 1004a (e.g., not orthogonal to or parallel with the body of the first stent frame 1004a) such that vascular flow through the stent frames 1004 tends to push the first stent frame 1004a in the same general direction in which the medial turns are pointed (e.g., outward from the body of the first stent frame 1004a). Accordingly, the medial turns 804 can increase the engagement force on the second stent frame 1004b as a result of the force of vascular flow.

In further aspects of the present technology, one or more of the stent frames 1004 can include two sets of medial turns 804 with opposing orientations such that blow flow and other forces in either direction on the stent frames 1004 cause one or both sets of medial turns 804 to embed more deeply into the accompanying stent frame 1004. Such interlocking stent frames 1004 (e.g., with one or more sets of medial turns 804) may be used to create a continuous flow path through different portions of vascular anatomy. For example, a first stent frame 1004a can be placed within an iliac artery or limb and connected to the second stent frame 1004b placed above or within an AAA.

Figure 12:
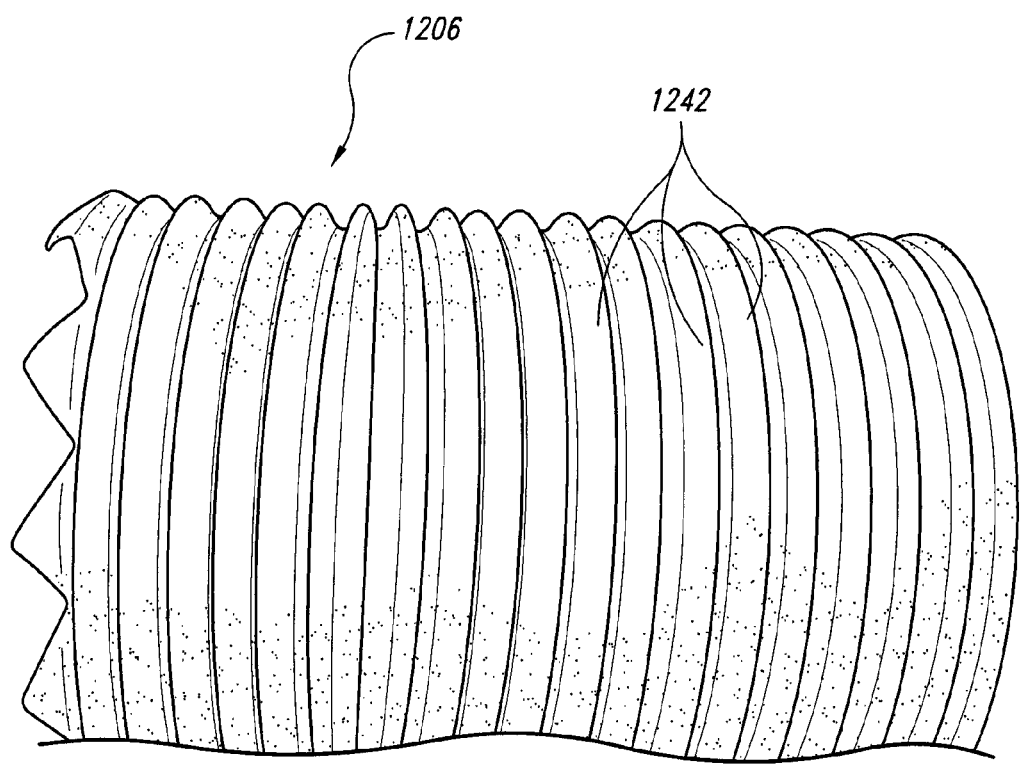
FIG. 12 is an enlarged side view of a portion of a cover for a stent graft configured in accordance with an embodiment of present technology.

FIG. 12 is an enlarged side view of a sleeve or cover 1206 for a stent graft configured in accordance with an embodiment of the present technology. In various embodiments, the cover 1206 can be positioned over a stent frame (e.g., as shown in FIGS. 1A and 1B) to define a flow path through one or more stent frames and facilitate the interlocking of stent frames. In the illustrated embodiment, the cover 1206 includes a plurality of circumferential ribs 1242 such that the cover 1206 has an undulating profile that can extend and contract during delivery (e.g., extend to a low-profile, sheathed configuration) and deployment (e.g., expand to a deployed configuration). During expansion, the ribs 1242 of the cover 1206 can mate with ribs 1242 of an opposing cover and interface with vessel walls to enhance the seal and fixation between stent grafts (e.g., the stent grafts 102 of FIGS. 1A and 1B) and between the stent graft and the arterial walls. For example, the apices of the ribs 1242 at the septal wall of a stent graft can interface or mate with the troughs of the corresponding ribs 1242 on a cover of an opposing stent graft. Additionally, the ribs 12 at the outer wall 112 can contact the arterial walls in a manner that at least substantially seals them together.

The cover 1206 can be made from a substantially impermeable, biocompatible, and flexible material. For example, the cover 1206 can be made from synthetic polymers, polyurethanes, silicone materials, polyurethane/silicone combinations, rubber materials, woven and non-woven fabrics such as Dacron®, fluoropolymer compositions such as a polytetrafluoroethylene (PTFE) materials, expanded PTFE materials (ePTFE) such as TEFLON®, GORE-TEX®, SOFT-FORM®, IMPRA®, and/or other suitable materials. Additionally, in some embodiments, the cover 1206 can be made from a material that is sufficiently porous to permit ingrowth of endothelial cells. Such a porous material can provide more secure anchorages of stent grafts and potentially reduce flow resistance, sheer forces, and leakage of blood around the stent grafts.

In various embodiments, the cover 1206 can be attached to a stent frame using a suture material. For example, the zigzagged end portions of the cover 1206 can be sutured to the stent frame. In other embodiments, the suture material may be distributed along the axial length of the stent frame (e.g., following diamond braid pattern) such that the suture material is not distributed in one cross section of the stent graft.

Stent Graft Delivery Systems Having Stent Covers

Figure 13:
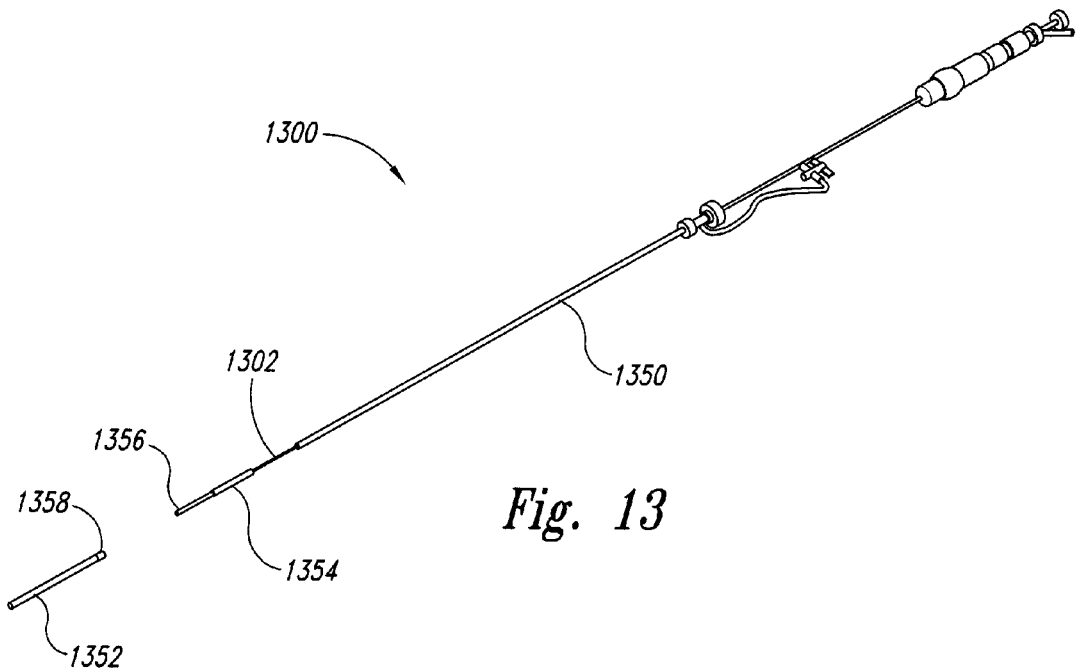
FIG. 13 is an exploded isometric view of a stent graft delivery system configured in accordance with another embodiment of the present technology.
Figure 14:
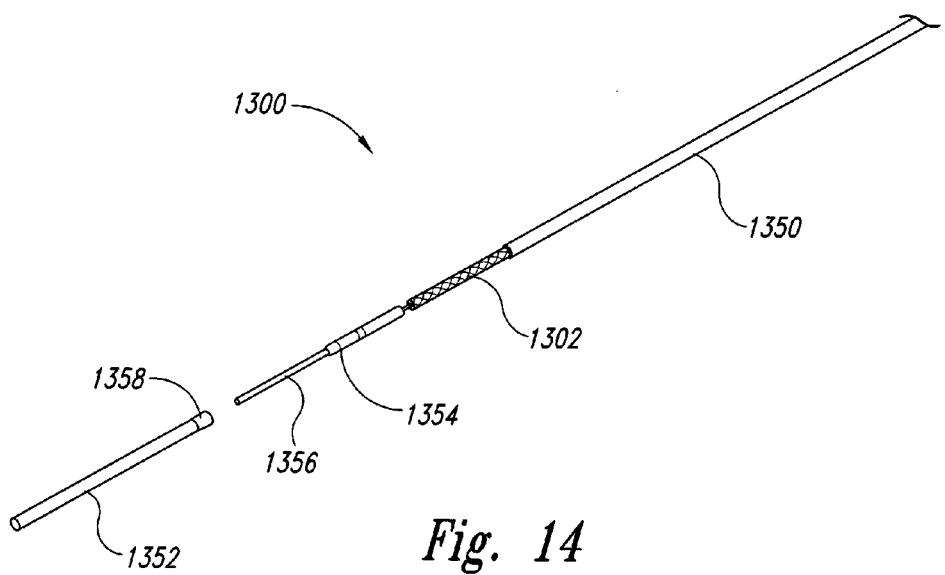
FIG. 14 is an enlarged exploded isometric view of a distal portion of the stent graft delivery system of FIG. 13.

FIG. 13 is an exploded isometric view of a stent graft delivery system 1300 ("delivery system 1300") configured in accordance with another embodiment of the present technology, and FIG. 14 is an enlarged exploded, isometric view of a distal portion of the delivery system 1300. Referring to FIGS. 13 and 14 together, the delivery system 1300 can include an outer sheath 1350, a stent graft 1302 (e.g., the stent grafts 1350, 202 and 702 described above with reference to FIGS. 1A-7B), a distal delivery component 1352, and a stent cover 1354. During assembly of the delivery system 1300, the stent graft 1302 can be held in place at both its proximal and distal end portions by the outer sheath 1350 and the distal delivery component 1354, respectively. The outer sheath 1350 and the distal delivery component 1354 can be referred to collectively as the delivery device. The distal delivery component 1354 can include a distal outer sheath (not shown) configured to cover a distal portion of the stent graft 1302 and/or a central wire 1356 positioned through the stent graft 1302 to navigate the vasculature and/or manipulate the distal outer sheath. In various embodiments, the stent graft 1302 can be only partially sheathed, leaving a portion of the stent graft 1302 (e.g., 3 inches of the stent graft 1302) exposed. The stent cover 1352 can be placed over the stent graft 1302 after it is loaded in the delivery device (see, e.g., FIG. 15). The stent cover 1352 sheathes the stent graft 1302 and a portion of the delivery device during shipping and storage, and assists in introducing the stent graft 1302 through an introducer valve and sheath during clinical use.

As further shown in FIGS. 13 and 14, the stent cover 1352 can be a tubular cylinder with a flared proximal end portion 1358. In selected embodiments, the stent cover 1352 can have an inner diameter of approximately 13 Fr and an outer diameter that fits into a 14 Fr introducer valve (e.g., approximately 0.220 inch). The stent cover 1352 can have various lengths (e.g., approximately 4 inches) suitable for sheathing a portion or all of the stent graft 1302. The flared proximal end portion 1358 can be approximately 0.260 inch in diameter and 0.25 inch long. In other embodiments, the stent cover 1352 can have larger or smaller inner and/or outer diameters, a differently sized flared proximal end portion 1358, and/or longer or shorter lengths.

The stent cover 1352 can be made from high density polyethylene (HDPE), low density polyethylene (LDPE), fluorinated ethylene propylene (FEP), polytetrafluoroethylene (PTFE), ethylene tetrafluoroethylene (ETFE), combinations thereof, and/or other suitable materials. In selected embodiments, the stent cover 1352 can include a liner along the inner diameter made of a material having a low coefficient of friction, such as FEP and PTFE. This can reduce frictional forces as the stent graft 1302 is loaded into the stent cover 1352 (e.g., during manufacturing) and during clinical use of the delivery system 1300.

Figure 15:
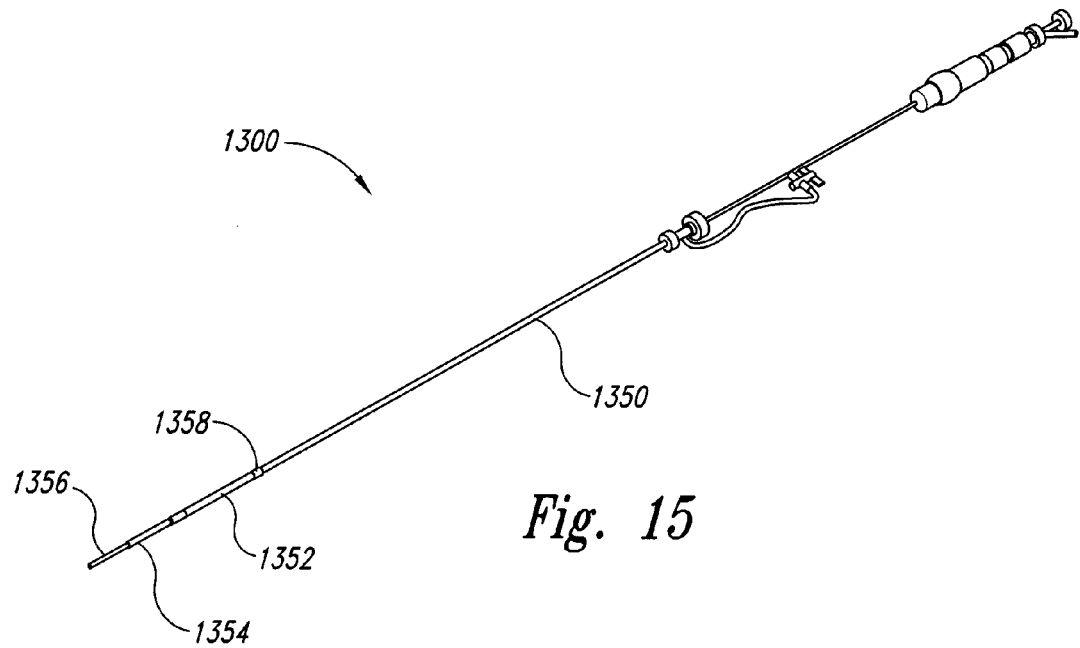
FIG. 15 is an isometric view of the stent graft delivery system if FIGS. 13 and 14 assembled in accordance with an embodiment of the present technology.

The funnel shape of the flared proximal end portion 1358 can facilitate loading the stent graft 1302 into the stent cover 1352 by gradually compressing fabric (e.g., Dacron®) or other materials on the outer surface of the stent graft 1302 (e.g., a ribbed cover as shown in FIG. 12) as it is inserted into the stent cover 1352. Once positioned over the stent graft 1302 (e.g., as shown in FIG. 15), the stent cover 1352 can maintain the sheathed size of the stent graft 1302 before deployment. In various embodiments, for example, the stent cover 1352 can be positioned over the stent graft 1302 during manufacture to prevent an outer layer of accordion-like folded Dacron®, PTFE, and/or other folded fabric from unfolding or unwrapping over time. Accordingly, the stent cover 1352 maintains a low profile of the stent graft 1302 such that it can be introduced into a small introducer sheath (e.g., a 10 Fr, 12 Fr, 14 Fr sheath), and therefore allows for percutaneous delivery of the stent graft 1302. By maintaining the low profile of the stent graft 1302, the stent cover 1352 also decreases the forces necessary to deploy the stent graft 1302, thereby increasing control and precision during deployment. Additionally, the stent cover 1352 can be used to house different sizes of stent grafts. This reduces or eliminates the need to increase the size of the introducer sheath for the larger stent grafts, and allows for the use of a 10 Fr, 12 Fr, 14 Fr, etc. introducer valve and sheath even when the stent graft size increases.

Figure 16:
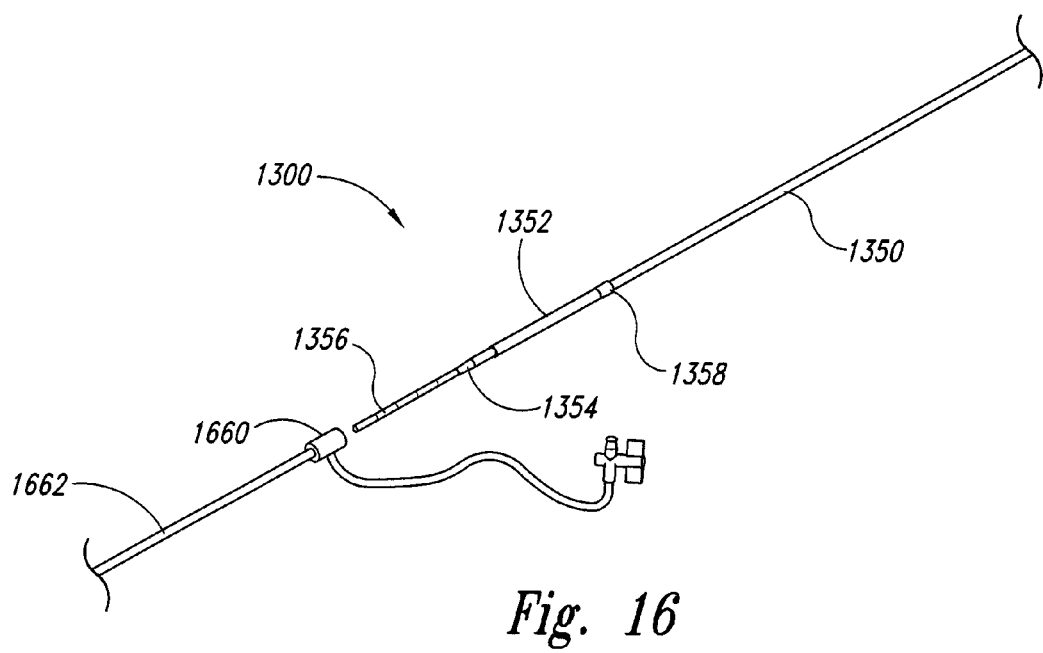
FIGS. 16-18 are enlarged, isometric views of a stent graft delivery system as it is being pushed through an introducer valve in accordance with an embodiment of the present technology.
Figure 17:
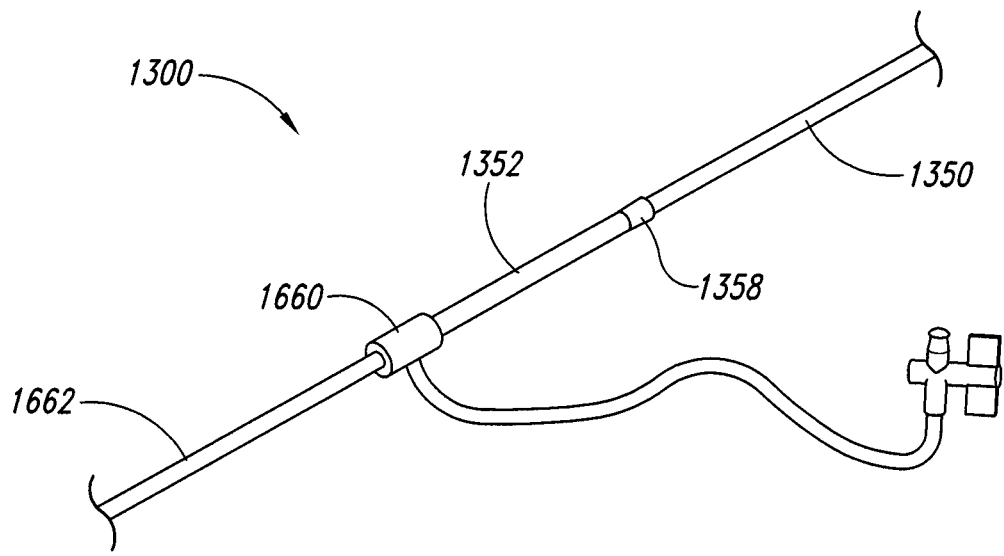
Figure 18:
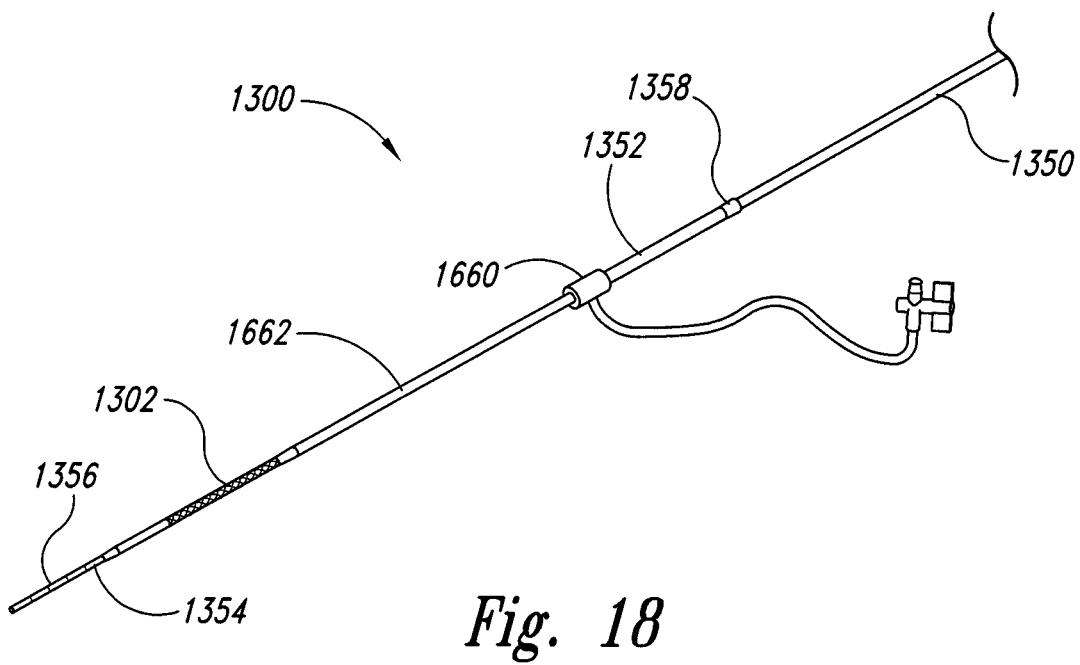

FIGS. 16-18 are enlarged, isometric views of various stages of the delivery system 1300 as it is being pushed through an introducer valve 1660 in accordance with an embodiment of the present technology. As shown in FIGS. 16 and 17, the delivery system 1300 can be inserted into the introducer valve 1660 and introducer sheath 1662 via the distal delivery component 1354 (FIG. 16), and is pushed through the introducer valve 1660 into the introducer sheath 1662 (FIG. 17). As discussed above, the stent cover 1352 provides sheathing for the stent graft as it is being delivered to the introducer valve 1660 such that the stent graft 1302 maintains a low profile. As shown in FIGS. 17 and 18, the stent cover 1352 can stop inside the introducer valve 1660 (e.g., by abutting an inner surface of the introducer valve 1660) to allow the stent graft 1302, the outer sheath 1350, and the distal delivery component 1354 to continue through the introducer valve 1660 into the introducer sheath 1662 to the site of the aneurysm. The stent graft 1302 is, therefore, partially exposed (e.g., approximately 3 inches of the stent graft 1302) as it passes through the introducer valve 1660, but the low profile provided by the stent cover 1352 allows it to be introduced into a small introducer sheath (e.g., a 14 Fr introducer sheath, a 10 Fr introducer sheath, etc.).

From the foregoing, it will be appreciated that specific embodiments of the technology have been described herein for purposes of illustration, but that various modifications may be made without deviating from the disclosure. Certain aspects of the new technology described in the context of particular embodiments may be combined or eliminated in other embodiments. Additionally, while advantages associated with certain embodiments of the new technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein. Thus, the disclosure is not limited except as by the appended claims.

We claim:

1. A method of delivering a stent graft, the method comprising:
   delivering to an aortic aneurysm a stent graft with a proximal sheath covering a proximal portion of the stent graft and a distal sheath covering a distal portion of the stent graft;
   positioning the distal portion of the stent graft above the aortic aneurysm;
   retracting the proximal sheath while simultaneously advancing a proximal portion of the stent graft to deploy the proximal portion of the stent graft, wherein the proximal sheath is retracted and the proximal portion of the stent graft is advanced at rates corresponding to a ratio of a deployed configuration length of the stent graft to a delivery configuration length of the stent graft;
   advancing the distal sheath relative to the stent graft to deploy the distal portion of the stent graft via a central wire; and
   retracting the distal sheath through an inner lumen formed by the stent graft.

2. The method of claim 1 wherein retracting the proximal sheath further comprises maintaining a constant position of the distal portion of the stent graft while the proximal portion is deployed.

3. The method of claim 1 wherein advancing the distal sheath further comprises maintaining a constant position of the proximal portion of the stent graft while the distal portion is deployed.

4. The method of claim 1 wherein advancing the distal sheath relative to the stent graft further comprises deploying anchoring barbs on the distal portion of the stent graft.

5. The method of claim 1, further comprising positioning the stent graft in a stent cover having an inner diameter of at most 14 Fr.

6. The method of claim 5, further comprising:
    positioning the stent cover in an introducer valve, wherein the introducer valve is no greater than 14 Fr; and
    advancing the stent graft from the stent cover into an introducer sheath via the introducer valve.
7. The method of claim 1 wherein the stent graft comprises a first stent frame, and wherein the method further comprises:
    delivering the first stent frame proximate an aneurysmal region, wherein the first stent frame includes openings;
    delivering a second stent frame to the first stent frame, the second stent frame having a braid pattern forming a body, the braid pattern having end turns at each of two ends of the second stent frame, and the braid pattern further having medial turns between the two ends of the second stent frame, wherein the medial turns form protrusions extending outward from the body of the second stent frame;
    positioning the medial turns of the second stent frame within the first stent frame; and
    expanding the second stent frame concentrically within the first stent frame, whereby the medial turns of the second stent frame interlock with the openings of the first stent frame.
8. The method of claim 1 wherein retracting the proximal sheath relative to the stent graft comprises retracting the proximal sheath with a gear arrangement.
9. The method of claim 1 wherein retracting the proximal sheath comprises only partially removing the proximal sheath from the stent graft, and wherein the method further comprises adjusting the distal sheath after only partially removing the proximal sheath.
10. The method of claim 9, further comprising retracting the distal portion of the stent graft.
11. The method of claim 10 wherein retracting the distal portion of the stent graft relative to the proximal sheath comprises retracting the distal portion of the stent graft with a gear arrangement.
12. The method of claim 10 wherein retracting the distal portion of the stent graft relative to the proximal sheath comprises moving a spur-shaped element on a tube engaged with the distal portion of the stent graft.
13. A method of delivering a stent graft, the method comprising:
    delivering, to a deployment location, a stent graft with a sheath covering at least a distal portion of the stent graft;
    positioning the stent graft at the deployment location;
    retracting the stent graft with one of a proximal or the distal end portions of the stent graft held in place while simultaneously advancing the sheath relative to the stent graft to deploy at least a proximal portion of the stent graft via a central wire, wherein the distal portion of the stent graft is retracted and the sheath is advanced at rates corresponding to a ratio of a deployed configuration length of the stent graft to a delivery configuration length of the stent graft; and
    retracting the sheath through an inner lumen formed by the stent graft.
14. The method of claim 13 wherein advancing the sheath comprises advancing the sheath with a gear arrangement.
15. The method of claim 13 wherein advancing the sheath further comprises maintaining a position of the proximal portion of the stent graft while the proximal portion is deployed.
16. The method of claim 13 wherein retracting the distal portion of the stent graft comprises moving a spur-shaped element on a tube engaged with the distal portion of the stent graft.

* * * * *

UNITED STATES PATENT AND TRADEMARK OFFICE
CERTIFICATE OF CORRECTION

PATENT NO.           : 8,858,613 B2                                   Page 1 of 1
APPLICATION NO.      : 13/237822
DATED                : October 14, 2014
INVENTOR(S)          : Andrew H. Cragg et al.

It is certified that error appears in the above-identified patent and that said Letters Patent is hereby corrected as shown below:

Title Page, item (56),

On page 5, in column 1, under "Other Publications", line 10, delete "Classicication," and insert -- Classification, --, therefor.

On page 5, in column 1, under "Other Publications", line 20, delete "Writton" and insert -- Written --, therefor.

In the Specification

In column 5, line 22, delete "intergrated" and insert -- integrated --, therefor.

Signed and Sealed this
Third Day of March, 2015

Michelle K. Lee
*Deputy Director of the United States Patent and Trademark Office*